USO10376374B2

(12) United States Patent
Biedermann et al.

(10) Patent No.: US 10,376,374 B2
(45) Date of Patent: Aug. 13, 2019

(54) INTERVERTEBRAL IMPLANT AND DEVICE FOR INSERTING AN INTERVERTEBRAL IMPLANT

(71) Applicants: Timo Biedermann, Trossingen (DE); Dimosthenis Dandanopoulos, Dauchingen (DE); Kevin Dold, Horb am Neckar (DE)

(72) Inventors: Timo Biedermann, Trossingen (DE); Dimosthenis Dandanopoulos, Dauchingen (DE); Kevin Dold, Horb am Neckar (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 209 days.

(21) Appl. No.: 15/246,448

(22) Filed: Aug. 24, 2016

(65) Prior Publication Data

US 2017/0056194 A1 Mar. 2, 2017

Related U.S. Application Data

(60) Provisional application No. 62/210,245, filed on Aug. 26, 2015.

(30) Foreign Application Priority Data

Aug. 26, 2015 (EP) .................................. 15182602

(51) Int. Cl.
*A61F 2/44* (2006.01)
*A61F 2/46* (2006.01)
*A61F 2/30* (2006.01)

(52) U.S. Cl.
CPC ............ *A61F 2/442* (2013.01); *A61F 2/4465* (2013.01); *A61F 2/4611* (2013.01);
(Continued)

(58) Field of Classification Search
CPC ...... A61F 2/442; A61F 2/4465; A61F 2/4611; A61F 2002/30242; A61F 2002/30538;
(Continued)

(56) References Cited

U.S. PATENT DOCUMENTS 8,673,012 B2    3/2014  Smith et al.
2007/0162129 A1 7/2007  Edie et al.
(Continued)

FOREIGN PATENT DOCUMENTS

DE   102008045174 A1   3/2010
EP     2 517 676 A1   10/2012
(Continued)

OTHER PUBLICATIONS

Extended European Search Report for Application No. 16185574.7 dated May 10, 2017, 7 pages.
Extended European Search Report for Application No. 15182602.1, dated Mar. 4, 2016, 8 pages.

*Primary Examiner* — Zade Coley
*Assistant Examiner* — Jessica Weiss
(74) *Attorney, Agent, or Firm* — Lewis Roca Rothgerber Christie LLP

(57) ABSTRACT

An intervertebral implant has a hollow space formed within the implant and accessible through an elongate opening extending through a recessed portion of the side wall, and the hollow space is shaped to receive an engagement portion of a drive shaft of an insertion tool; and the intervertebral implant includes at least two guiding surfaces facing each other and being configured for sliding engagement by a portion of a sleeve of the insertion tool movably holding the drive shaft.

32 Claims, 18 Drawing Sheets

(52) U.S. Cl.
CPC ............ *A61F 2002/30242* (2013.01); *A61F 2002/30378* (2013.01); *A61F 2002/30426* (2013.01); *A61F 2002/30538* (2013.01); *A61F 2002/30772* (2013.01); *A61F 2002/30795* (2013.01); *A61F 2002/4475* (2013.01); *A61F 2002/4627* (2013.01); *A61F 2230/0028* (2013.01); *A61F 2310/00017* (2013.01); *A61F 2310/00023* (2013.01); *A61F 2310/00071* (2013.01)

(58) Field of Classification Search
CPC .. A61F 2002/30772; A61F 2002/30795; A61F 2002/4475; A61F 2002/4627; A61F 2310/00017; A61F 2310/00023; A61F 2310/00071
USPC ................. 623/17.11–17.16; 606/99–100
See application file for complete search history.

(56) References Cited

U.S. PATENT DOCUMENTS

| | | |
|---|---|---|
| 2007/0282441 A1 * | 12/2007 | Stream ............... A61B 17/92 623/17.11 |
| 2011/0276142 A1 | 11/2011 | Niemiec et al. |
| 2012/0165943 A1 | 6/2012 | Mangione et al. |
| 2014/0172103 A1 | 6/2014 | O'Neil et al. |

FOREIGN PATENT DOCUMENTS

| | | | | |
|---|---|---|---|---|
| EP | 2535021 | A1 | 12/2012 | |
| EP | 2535022 | A1 | 12/2012 | |
| FR | 3016285 | * | 1/2014 | ............ A61F 2/44 |
| FR | 3 016 285 | A1 | 7/2015 | |
| TW | 201424674 | A | 7/2014 | |
| WO | WO 2015/081142 | A1 | 6/2015 | |

* cited by examiner

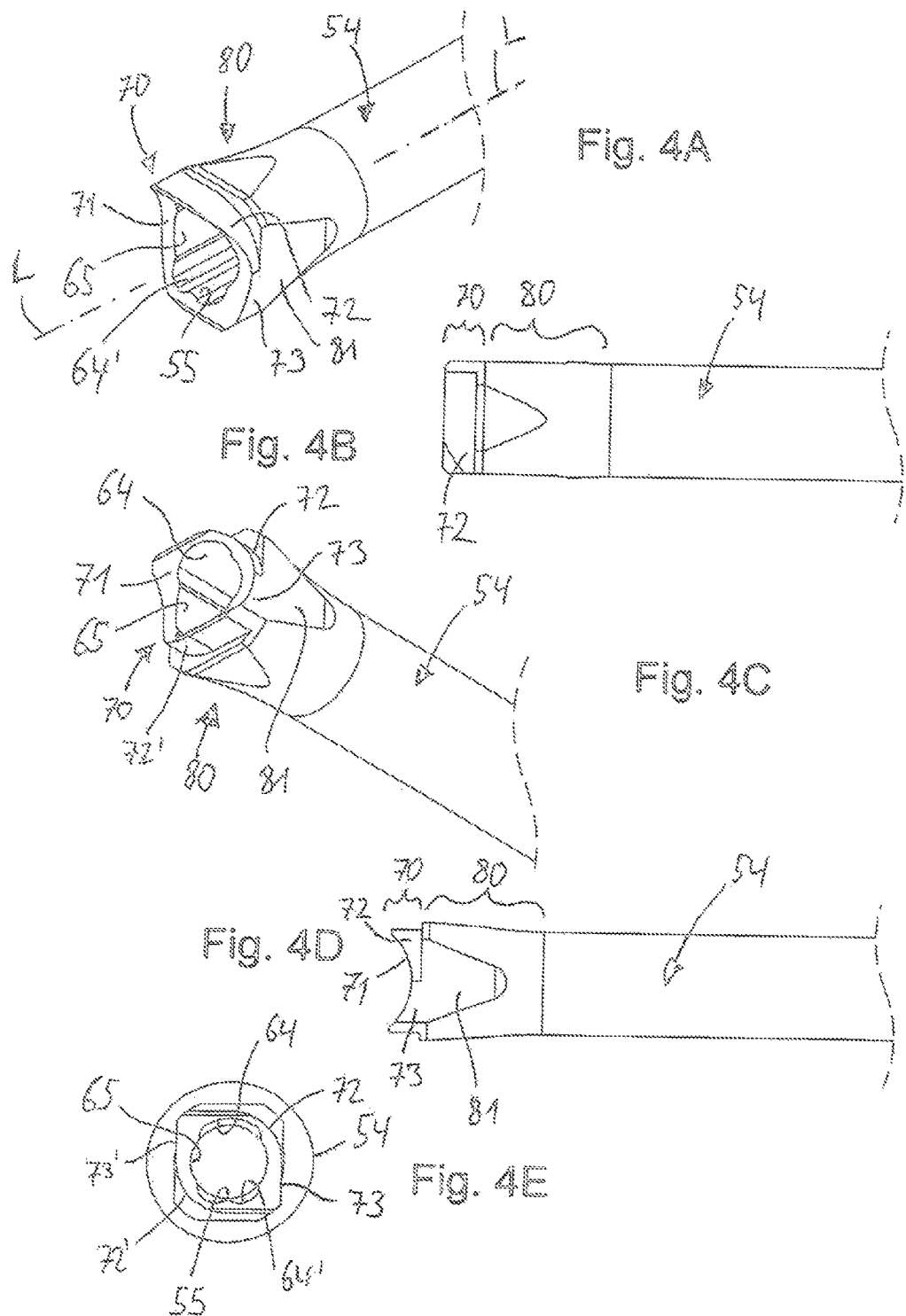

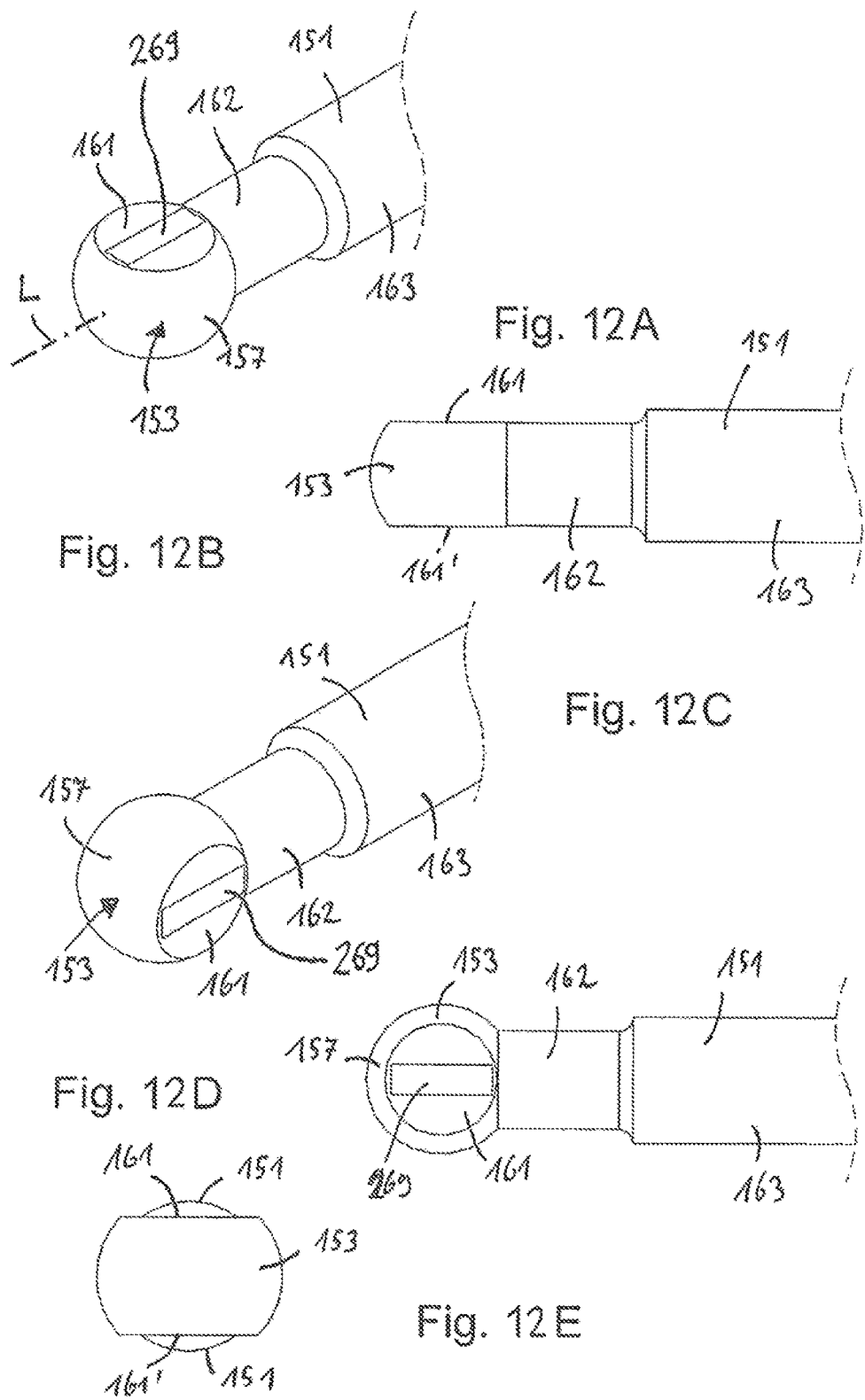

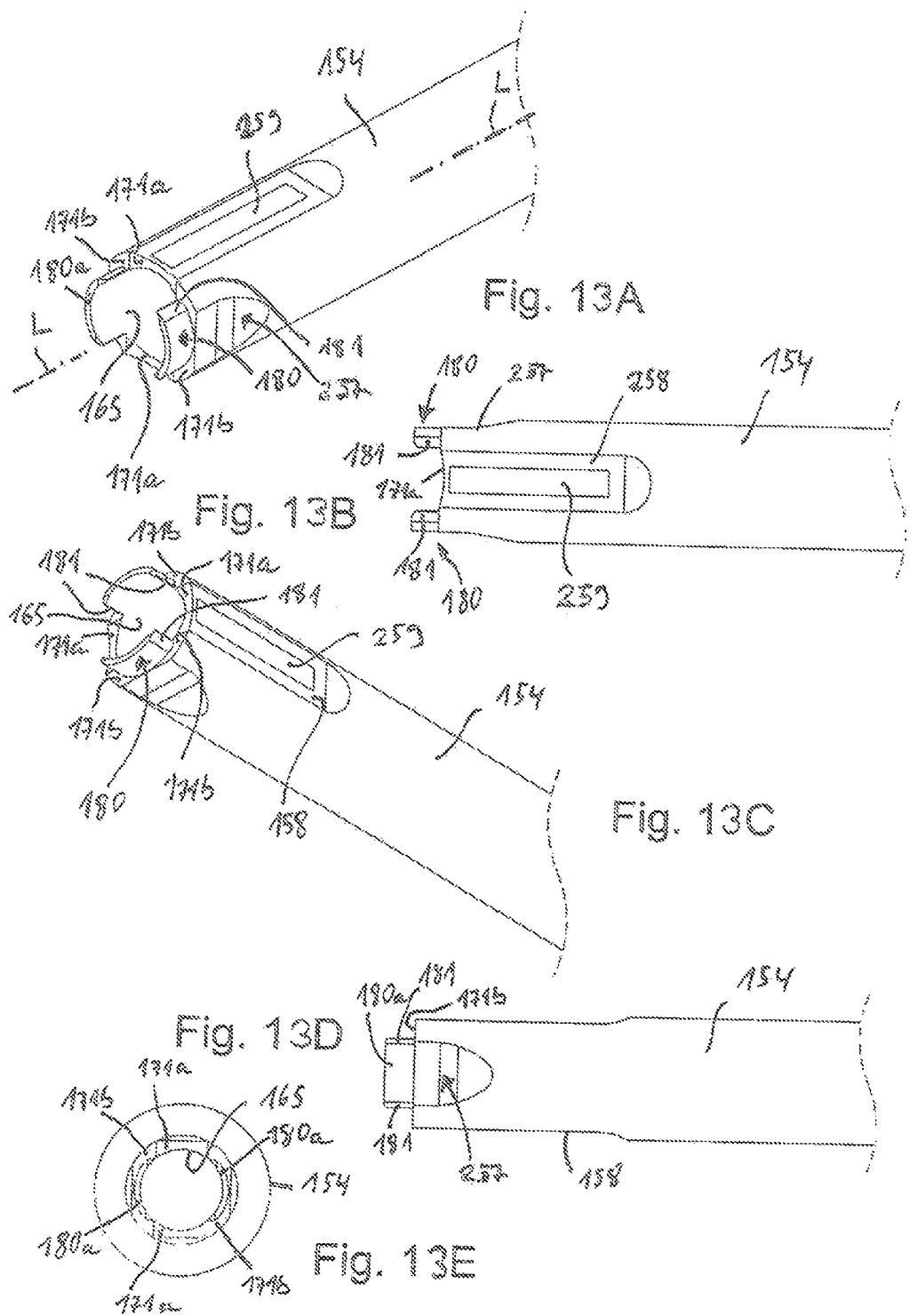

INTERVERTEBRAL IMPLANT AND DEVICE FOR INSERTING AN INTERVERTEBRAL IMPLANT

CROSS-REFERENCE TO RELATED APPLICATIONS

This application claims the benefit of U.S. Provisional Patent Application Ser. No. 62/210,245, filed on Aug. 26, 2015, and also claims priority to European Patent Application No. 15 182 602.1, filed on Aug. 26, 2015, the entire content of each of which is hereby incorporated by reference.

BACKGROUND

The present invention relates to an intervertebral implant having a top surface configured to engage a first vertebral body, a bottom surface configured to engage a second vertebral body and a side wall connecting the top surface and the bottom surface, and a hollow space formed within the implant and accessible through an elongate opening extending through a portion of the side wall.

The invention further relates to a device for inserting the intervertebral implant into a body, comprising a drive shaft including an engagement portion for engaging a hollow space of an intervertebral implant in a form-fit connection, and a sleeve movably guiding the drive shaft and having a longitudinal axis.

An intervertebral implant which is configured to be engaged by an insertion device for insertion of the implant between first and second vertebral members is known from DE 10 2008 045 174 A1. The intervertebral implant has an insertion opening including a slit-like elongated shape that extends through the side wall. The insertion opening provides access to an inner space of the implant for the insertion device. The insertion device has a sleeve and a shaft guided through the sleeve, wherein an elongate support projection having a cylindrical support surface is provided at a distal end of the shaft.

The shaft can be rotated with respect to the sleeve, such that the elongate support projection is first inserted through the slit-like opening into the inner space and then rotated to establish a connection. The shaft may then be drawn back with respect to the sleeve in order to connect the cylindrical support surface of the shaft with a corresponding cylindrical recess formed at an inner wall of the inner space in a direction transverse to the insertion opening in a form-fit manner. This connection allows for rotating and selectively positioning the implant with respect to the insertion tool, wherein its shaft follows the path of the slit-like opening. A counterforce and sliding engagement is achieved by an appropriately shaped front wall of the distal end and of the sleeve, which engages the side wall of the implant around the insertion opening.

Another insertion device, which has a shaft-like section that may be rotated after insertion to establish a connection between the device and an intervertebral implant, is disclosed in US 2007/0162129 A1. At the distal end of the shaft, an elongated head having a cuboid shape is provided. Drawing back the distal end then sandwiches an outer wall of the implant between a back side surface of the cuboid-Ss shaped elongate head and a stop provided at distal end of a sleeve-like first section of the device.

U.S. Pat. No. 8,673,012 B2 also discloses an intervertebral spacer which in FIGS. 8A-C thereof has an inner cavity and a through hole, through which a portion of an insertion tool having transverse extensions may be inserted and then rotated, to establish a connection between a trailing end of the intervertebral spacer and the insertion tool. Thereby, an appropriately shaped front wall of the insertion tool having engagement features is pressed onto a side wall of the intervertebral spacer.

Documents EP 2 535 021 A1 and EP 2 535 022 A1 provide other examples of devices suitable for insertion of an intervertebral implant into a body following transforaminal lumbar interbody fusion surgery techniques (TLIF). The TLIF technique involves approaching the spine from the side of the spinal canal through a midline incision in the patients back. This approach greatly reduces the amount of surgical muscle dissection and minimizes the nerve manipulation required to access the vertebrae, discs and nerves.

SUMMARY

According to aspects of embodiments of the invention, an intervertebral implant and/or a device for inserting an intervertebral implant and/or a system comprising an intervertebral implant and a device for inserting the same that is simplified in terms of its use and in view of the possibilities of final positioning are provided.

Aspects and features of embodiments of the invention, including an intervertebral implant, a device for inserting the intervertebral implant into a body, and a system comprising the intervertebral implant and the device for inserting the same, are described herein with respect to some exemplary embodiments and are set forth in the claims.

According to one or more embodiments of the invention, an intervertebral implant is provided wherein a sidewall connecting respective top and bottom surfaces includes a portion which is recessed or set back from an outer contour of the implant.

This recessed portion includes an elongate opening suited for insertion of an engagement portion of a drive shaft of an insertion tool into a hollow space provided within the implant. The outer contour of the implant defines at least two guiding surfaces facing one another and configured for sliding engagement by a portion of a sleeve of the insertion tool.

Thus, a connection between the implant of these embodiments and a device for insertion of the intervertebral implant into a body is improved in that there is not or not only established a force acting onto the (recessed) side wall but (also) on one or more engagement surfaces facing a recess. Hence, the guiding stability of the implant being engaged by a respective insertion device is enhanced and failure of the connection is avoided.

In one or more embodiments, the engagement surfaces are provided at extensions of the top and/or bottom surfaces, respectively, which extend beyond an intersection of the recessed portion of the side wall and the top and bottom surfaces, respectively. The outer edges of the extensions form the outer contour of the implant at this location, from which the recessed portion is then set back to form a channel extending between the extensions.

Embodiments of the implant may include a hollow space which is shaped to receive an engagement portion of a drive shaft of an insertion tool in a first state of insertion. The hollow space allows to establish a form-fit connection with a complementarily shaped engagement portion of the insertion device. In view of the form-fit connection no sandwiching or compression of a thin side wall between the engagement portion of the drive shaft and a front wall or stop at the distal end of the sleeve is necessary. This allows to define small dimensions of the hollow space within the implant, for example only in a trailing end of the implant.

As a full form-fit connection is established between the hollow space and the engagement portion, further connection structures such as above described engagement surfaces may be specifically adapted to other applications than simple fixation of the implant. For example, guiding surfaces may help in guiding and sliding engagement structures of the sleeve of an insertion tool. Alternatively or additionally, engagement structures of the insertion device may be adapted to prevent removal of the engagement portion from the form-fit connection. Still further, engagement structures of the insertion device may be adapted to the guiding surfaces such as to improve handling of the implant by defining a single-sided rotation, as will be described below.

In one or more embodiments, the hollow space is spherical. When the engagement portion of the insertion tool is also at least partially spherical as well, a connection in the form of a ball joint is established.

Further, according to embodiments of the invention, a device for inserting an intervertebral implant into a body comprises a drive shaft, which includes an engagement portion for engaging a hollow space of an intervertebral implant, and a sleeve movably holding and guiding the drive shaft and having a longitudinal axis. The sleeve comprises at a first end thereof a first engagement structure, and adjacent the first engagement structure a second engagement structure.

As in the embodiments above regarding the implant, the engagement portion of the insertion device may, for example, have a shape corresponding to that of a hollow space to provide a form-fit connection. Further, the shape of an engagement portion may be flattened such as to allow passing the same through an elongate opening of the implant prior to establishing the form-fit connection.

For example, if the engagement portion has a partially spherical shape, segments may be removed from a sphere on opposite sides thereof in order to obtain two flat parallel planes on opposite sides of the sphere, which extend also parallel to the longitudinal axis of the sleeve of the insertion device, which axis defines the direction of insertion. Both the hollow space and the engagement portion have a simple structure, are easy to manufacture, and provide a stable, large contact area form-fit connection.

The first engagement structure of the sleeve may engage the at least one guiding surface of the recessed portion of the side wall of the intervertebral implant as described above, when the engagement portion is received in the hollow space in a first state of insertion. Thereby, the first engagement structure is shaped to allow rotation of the sleeve and the drive shaft by an angle α about the longitudinal axis to transfer the engagement portion into a second state. In the second state the engagement portion is supported in a form-fit connection in the hollow space.

The second engagement structure of the sleeve may engage the guiding surfaces of the recessed portion, when the engagement portion is supported in the hollow space in the second state and the first engagement structure is moved toward the recessed portion. Thereby, unlike the first engagement structure, the second engagement structure is shaped to prevent rotation of the sleeve and the drive shaft about the longitudinal axis, thus defining a third state of connection.

Since there are two engagement structures positioned adjacent each other, an adjustment of the guiding sleeve with respect to the drive shaft and implant allows to bring the engagement structures in contact with the engagement surfaces of the implant in a sequential manner. Both engagement structures differ from each other in that the first engagement structure allows rotation of the sleeve while the second engagement structure prevents rotation. In other words, the first engagement structure allows establishing the form-fit connection by rotation, and the second engagement structure locks or secures the form-fit connection (the third or locked state).

In one embodiment, the third or locked state may be indicated to the operator by a knob provided, for example, at the handle, which is indicative of the position of the sleeve with respect to the drive shaft, and thus with respect to the implant, which may be hidden inside the body during surgery.

According to further embodiments, the rotation by the first engagement structure may be limited by one or more stops to provide a single-sided rotation only. This stop may define just one direction of rotation each for transferring the insertion tool from the first state into the second state and vice versa, respectively. A particular advantage arises thereby in that the operator has to deal with only two different angular positions of the instrument (rotated left and rotated right).

Hence, the angular position of the instrument as well as the position of the knob allow the operator to know in which of the three connection states the implant currently is (inserted, form-fit connected, or locked).

According to one or more embodiments, the implant and the device are particularly configured for a transforaminal lumbar interbody fusion surgery (TLIF), the implant having a kidney-shape, a leading end and a trailing end, the hollow space, the elongate opening, and the recessed portion of the side wall as well as the engagement surfaces being provided at the trailing end.

In a second embodiment there is provided only one first engagement structure at the sleeve thus facilitating a simple structure. Herein, rotation of the drive shaft with respect to the sleeve is permitted. The first engagement structure may engage the guiding surfaces of the intervertebral implant, when the engagement portion is received in the hollow space in a first state of insertion. In this first state, the first engagement structure already prevents rotation of the sleeve with respect to the implant. Next, the shaft is allowed to be rotated with respect to the sleeve by an angle α about the longitudinal axis to transfer the engagement portion of the shaft into a second state. In the second state the engagement portion is supported in a form-fit connection in the hollow space.

In the second embodiment, an outer contour of the implant in the region of the guiding surfaces may define a rounded portion and a portion recessed form the rounded shape, in particular a straight portion. The recessed or straight portion allows a latched-in state of the implant with respect to the device, which may correspond, for example, to a specific posture of the implant maintained during insertion of the implant towards the implant site. The latched-in state provides for a robust connection between the implant and the device and assists in maintaining the posture until the implant reaches the implant site and also provides a tactile response to the surgeon to indicate that the implant is now urged to rotate at the first end of the device.

BRIEF DESCRIPTION OF THE DRAWINGS

The invention will be best understood by the following detailed description of some embodiments taken in conjunction with the accompanying drawings. Therein.

FIG. 4A shows in a top perspective view a distal end portion of a guiding sleeve of the device shown in FIG. 2A;

FIG. 4B shows the same as FIG. 4A, but in a side view;

FIG. 4C shows the same as FIG. 4A, but in a bottom perspective view;

FIG. 4D shows the same as FIG. 4C, but in a side view;

FIG. 4E shows the same as FIG. 4A, but in a front view from the distal side;

FIG. 12A shows in a perspective view a distal end portion of a drive shaft of the device shown in FIG. 11A in a first state of insertion (implant not shown);

FIG. 12B shows the same as FIG. 12A, but in a side view;

FIG. 12C shows the same as FIG. 12A, but rotated by 90° into a second form-fit state (implant not shown);

FIG. 12D shows the same as FIG. 12C, but in a side view;

FIG. 12E shows the same as FIG. 12A, but in a front view from the distal side:

FIG. 13A shows in a top perspective view a distal end portion of a guiding sleeve of the device shown in FIG. 11A;

FIG. 13B shows the same as FIG. 13A, but in a top view;

FIG. 13C shows the same as FIG. 13A, but viewed from a different angle;

FIG. 13D shows the same as FIG. 13A, but in a side view;

FIG. 13E shows the same as FIG. 13A, but in a front view from the distal side;

DETAILED DESCRIPTION

Figure 1:
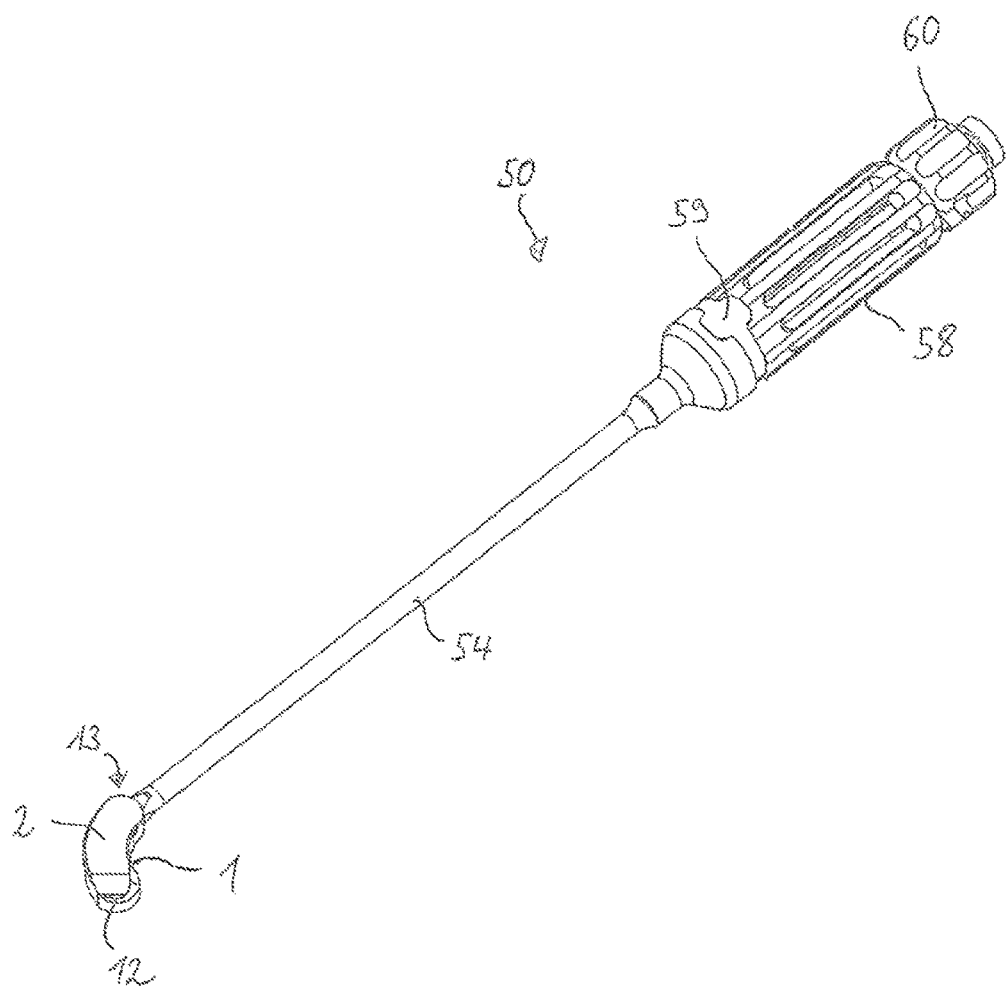
FIG. 1 shows in a perspective view an overview of an intervertebral implant held by a device for inserting the implant into a body according to one or more embodiments of the invention.

Embodiments both of an intervertebral implant as well as of a device for inserting an intervertebral implant into a body are further detailed with reference to FIGS. 1-9B. FIG. 1 shows in a perspective view an overview of an intervertebral implant 1 held by a device 50 for inserting the implant into a body, or, more specifically, into a space between two vertebrae of the vertebral column.

The device 50 includes a drive shaft 51 (see FIGS. 2A, 2B), a guiding sleeve 54, a handle 58, a resilient knob 59, and an adjusting means 60, which in an embodiment is an adjusting nut, which has an internal thread (not shown) that interacts with an external thread (not shown) at or near the proximal end of the drive shaft 51. The drive shaft 51 is movably guided within the sleeve 54 and can be advanced or retracted with respect to the sleeve by rotating the adjusting nut of the adjusting means 60. Other means to facilitate advancement or retraction of the drive shaft 51 with respect to the guiding sleeve 54 may be contemplated as well, and the invention is not limited to the specific embodiment.

As can be seen particularly from FIGS. 3A through 3E, which show details of the distal end of drive shaft 51, the drive shaft 51 comprises an engagement portion 53 having a partially spherical shape (spherical surface 57), wherein on opposite aides thereof, segments of the sphere are removed to yield flat surfaces 61, 61'. The flat surfaces 61, 61' provide for a flattened shape of the engagement portion 63 which allows introduction of the same through a narrow elongate opening 8 of the implant 1.

Figure 3A:
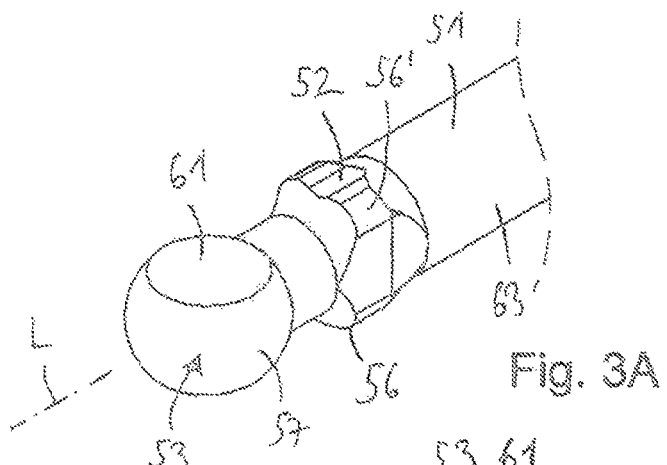
FIG. 3A shows in a perspective view a distal end portion of a drive shaft of the device shown in FIG. 2A in a first state of insertion (implant not shown)
Figure 3B:
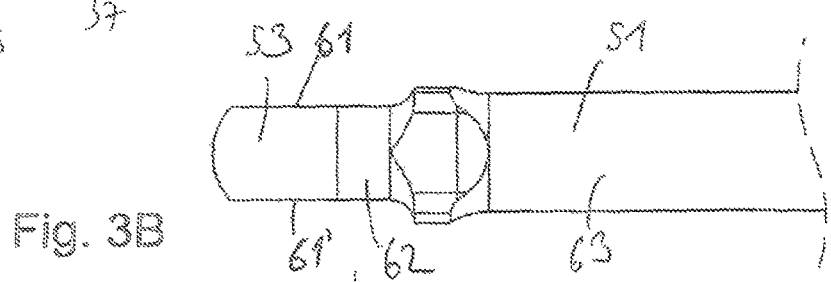
FIG. 3B shows the same as FIG. 3A, but in a side view.
Figure 3C:
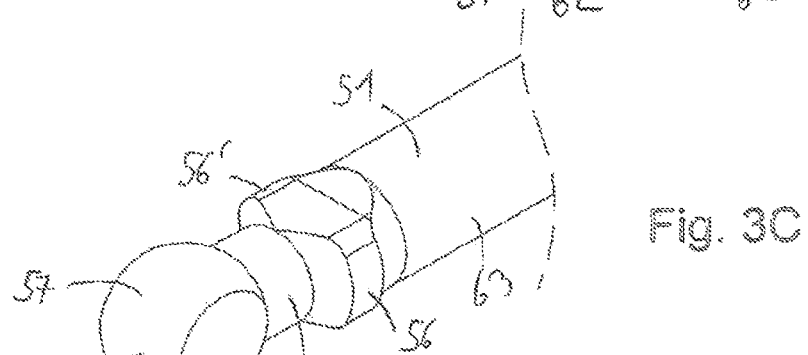
FIG. 3C shows the same as FIG. 3A, but rotated by 90° into a second form-fit state (implant not shown)
Figure 3D:
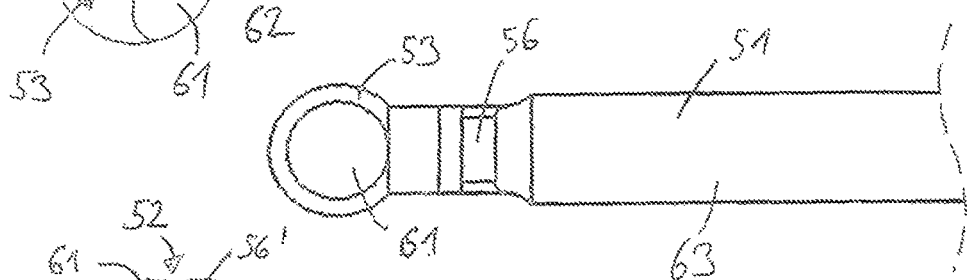
FIG. 3D shows the same as FIG. 3C, but in a side view.
Figure 3E:
FIG. 3E shows the same as FIG. 3A, but in a front view from the distal side.

The engagement portion 53 is connected to a main portion 63 of the drive shaft 51 via a neck portion 62, which has a diameter smaller than a diameter of the main portion 63. However, the diameter of the neck portion 62, which in an embodiment is cylindrical, is substantially the same as the width of the engagement portion 53 in a direction perpendicular to the opposite flat surfaces 61, 61', as can be seen in FIG. 3B.

The drive shaft 51 further has adjacent the neck portion 62 and at an end of the main portion 63 two opposite protrusions 56, 56' extending perpendicular to a longitudinal axis of the drive shaft 51. One of the protrusions (protrusion 58') is as provided with a longitudinal groove 52 extending along a portion of the drive shaft 51. The protrusions 56, 56' and the groove 52 interact with complementary features, such as recesses 64, 64' and a rib 55 provided in an inner bore 65 of the guiding sleeve 54 (see FIGS. 4A through 4E). As a result, the drive shaft 51 can be displaced with respect to the guiding sleeve 54 along a longitudinal axis L of the guiding sleeve 54 using the adjusting means 60 as noted above, but cannot be rotated with respect to the guiding sleeve 54.

Figure 2A:
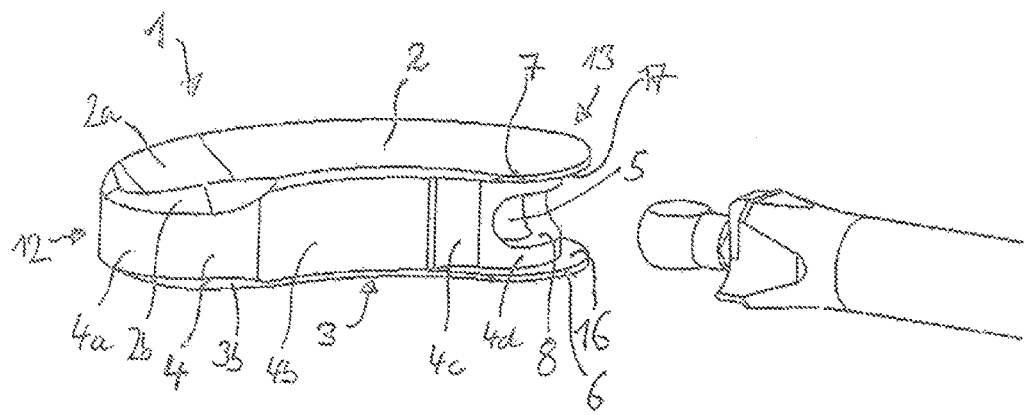
FIG. 2A shows an enlarged perspective view of the intervertebral implant and a distal end portion of the device as shown in FIG. 1 in a state prior to insertion.
Figure 2B:
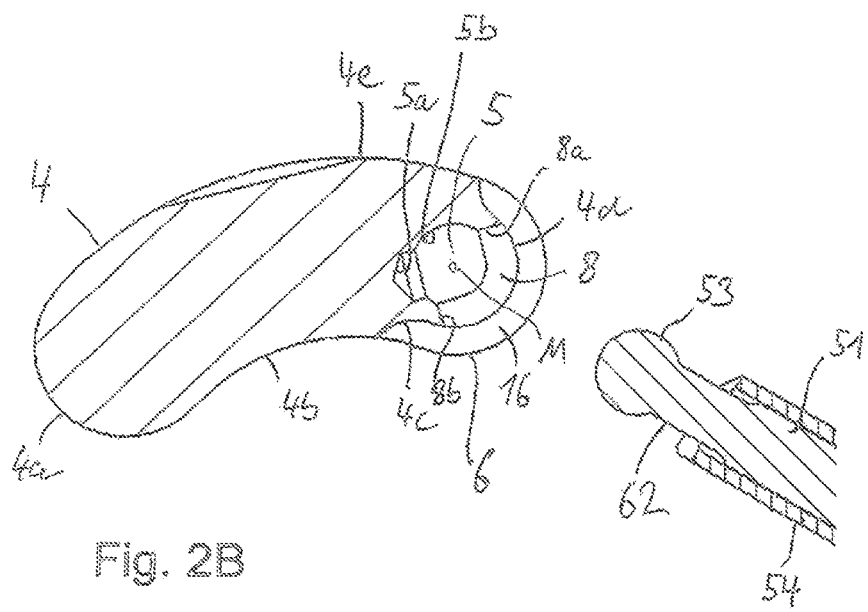
FIG. 2B shows the same as FIG. 2A, but in a cross-sectional top view.

As can be seen from FIGS. 1, 2A and 2B, the intervertebral implant 1 is substantially of a kidney shape and has a leading end 12 and a trailing end 13. The terms "leading" and "trailing" originate from the manner of placement Into the space between the vertebrae from a lateral side in this specific embodiment (which refers to a TLIF cage). The implant 1 has a top surface 2, a bottom surface 3, and a side wall 4 extending between the top and bottom surfaces 2, 3. The top and bottom surfaces 2, 3 are substantially planar and parallel to each other except inclined portions 2a, 2b, and 3b extending towards the leading end 12, which facilitates easier insertion between the vertebrae.

The side wall 4 comprises, in the example of the kidney-shaped TLIF cage, a cylindrical portion 4a at the leading end 12, a concave portion 4b on a lateral side, a substantially cylindrical recessed portion 4d at the trailing end 13, recessed transition portions 4c on both sides of the recessed portion 4d, and a convex portion 4e on the opposite lateral side.

The top surface 2 includes an edge with each of the portions 4a, 4b and 4e of the side wall 4 at the leading end 12 and the lateral sides of the implant 1. However, at the trailing end 13, the top surface 2 extends beyond the portions 4c and 4d of the side wall 4, which thus forms an overhanging extension 7 as can be seen in FIG. 2A. Similarly, the bottom surface 3 includes an edge with each of the portions 4a, 4b and 4e of the side wall 4 at the leading end 12 and the lateral sides of the implant 1. At the trailing end 13, the bottom surface 3 extends beyond the portions 4c and 4d of the side wall 4, which thus forms an overhanging extension 6 opposite the overhanging extension 7. As a result, portions 4c and 4d of the side wall 4 are recessed or set back from an outer contour of the implant 1, which is defined by the edges of the top and bottom surfaces 2 and 3 in this example, including the edges of the extensions 6 and 7.

As shown in FIG. 2A, the overhanging extensions 6 and 7 form surfaces 16, 17, respectively, due to the set back of the portions 4c, 4d of the side wall 4. More specifically, surfaces 16, 17 extend around the trailing end 13 in an arc-shaped manner and face towards each other with the recessed portions 4c, 4d of the side wall 4 extending therebetween. Thus, a channel or recess is formed in the outer contour at the trailing end 13 of the implant 1 between extension 6, 7, which is limited by portions 4c, 4d of the side wall 4 and the surfaces 16, 17 of the extensions 6, 7. Since the surfaces 16, 17 serve to guide and support engagement structures of the sleeve 54, as will be explained below, the surfaces 16, 17 are denoted in the following as guiding surfaces 16, 17. The guiding surfaces 16, 17 of the instant embodiment are parallel to each other, but may also be inclined or rounded.

As shown in FIG. 2A, an elongate opening 8 is formed within the cylindrically shaped recessed portion 4d of the side wall 4. The elongate opening has a horizontal length larger than its vertical height and extends across the portion 4d of the side wall 4 between a right side end or stop 8a and a left side end or stop 8b along a direction substantially parallel to the plane of the top and bottom surfaces 2 and 3.

The elongate opening 8 provides access to a hollow space 5 positioned adjacent the elongate opening 8 within the implant 1. The hollow space 5 has a shape of a sphere 5b. Moreover, the hollow space 5 has a diameter which is larger than the vertical height of the elongate opening 8. The hollow space 5 may, for example, be manufactured by furnishing a cylindrical core bore hole 5a first in the solid material within the implant 1, and then skimming the sphere 5b in a second step, thereby expanding the core bore hole 5a at an appropriate position adjacent the elongate opening 8 along the core bore hole 5a to the shape of the sphere 56, as can be seen in FIG. 2B. However, other manufacturing techniques of the implant such as rapid prototyping, mechanical or laser cutting, etc. are possible as well.

As can be seen particularly in the top view of FIG. 2B, the hollow space 5 has a symmetrical center point M of the sphere 5b, and the portion 4d of the side wall 4 as well as the guiding surfaces 16, 17 (in FIG. 2B, only the surface 16 is shown) are concentric about an axis A extending through the center point M. The axis A extends vertically through the implant through the center point M, and represents a rotation axis of the implant 1 with respect to the device 50. As will be described below, the recessed portion 4d and the guiding surfaces 16, 17 are engaged by the engagement structures 70, 80 provided at a distal end of the sleeve 54 when a connection is established between the device 50 and the implant 1 as shown in FIG. 1. The engagement may be a sliding engagement to allow for rotation and a range of angular positions of the implant 1 with respect to the device 50. Moreover, the guiding surfaces 16, 17 help in firmly supporting the engagement structures 70, 80 after engagement.

Returning to the description of the device 50, FIGS. 4A through 4E depict details of the engagement structures 70, 80 of the guiding sleeve 54. More specifically, the sleeve 54 is provided with a first engagement structure 70 and also with a second engagement structure 80 positioned adjacent each other at the distal end of the sleeve 54. In operation of the device 50 and implant 1, the first engagement structure 70 engages with the guiding surfaces 16, 17 in a first state of insertion illustrated in FIGS. 5A and 58 and in a second state, wherein a form-fit connection has been established as illustrated in FIGS. 6A and 6B, and the second engagement structure 80 engages with the guiding surfaces 16, 17 in a third state illustrated in FIGS. 7A and 7B, wherein the form-fit connection is secured or locked.

The first engagement structure 70 comprises a front wall 71 configured to be brought into contact with the recessed portion 4d of the side wall 4. The front wall 71 for this purpose has a complementary shape with respect to the recessed portion 4d, i.e., cylindrical in this embodiment.

The first engagement structure 70 further has two opposite outer rounded guiding faces 72, 72' each shaped as a segment of a cylinder. Outer rounded guiding faces 72, 72' extend about a quarter circle around the longitudinal axis L of the sleeve 54 and define a diameter which is substantially equal to the distance between the guiding surfaces 16, 17 of the implant 1. Accordingly, the first engagement structure 70 and the outer rounded guiding faces 72, 72' may be inserted into the channel defined between the guiding surfaces 16, 17 of implant 1.

The first engagement structure 70 further has two opposite stops or stop faces 73, 73' which are continuous with the outer rounded guiding faces 72, 72' but deviate from a cylinder shape towards larger radii. The stop faces 73, 73' in this embodiment correspond to parts of a cuboid shape. When seen from the front side, the stop faces 73, 73' provide a square profile while the rounded guiding faces 72, 72' provide a circular profile. As a result, a diameter between portions of the opposite stop faces 73, 73' extending through the longitudinal axis L is larger than the distance between the opposite guiding surfaces 16, 17 of the implant 1.

Figure 5A:
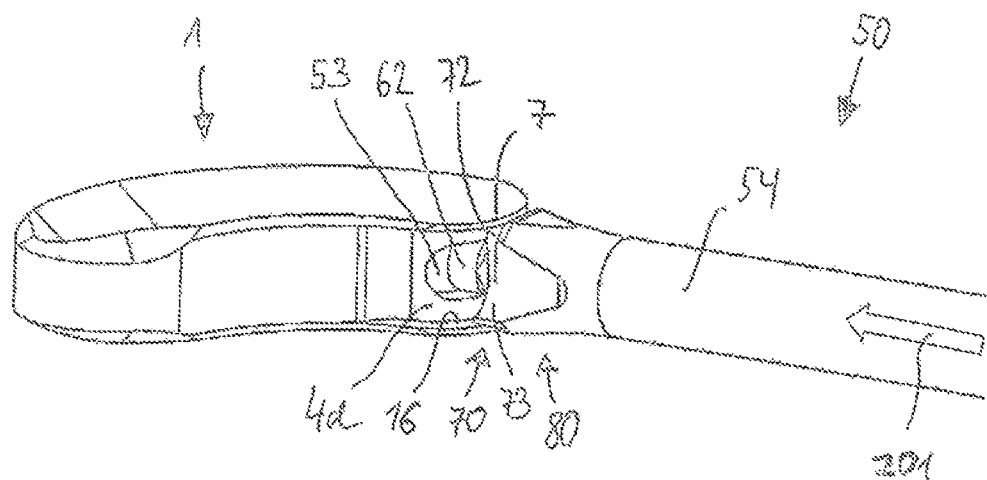
FIG. 5A shows the same as FIG. 5A, but in a first state of insertion of the drive shaft and engagement portion into the intervertebral implant.
Figure 5B:
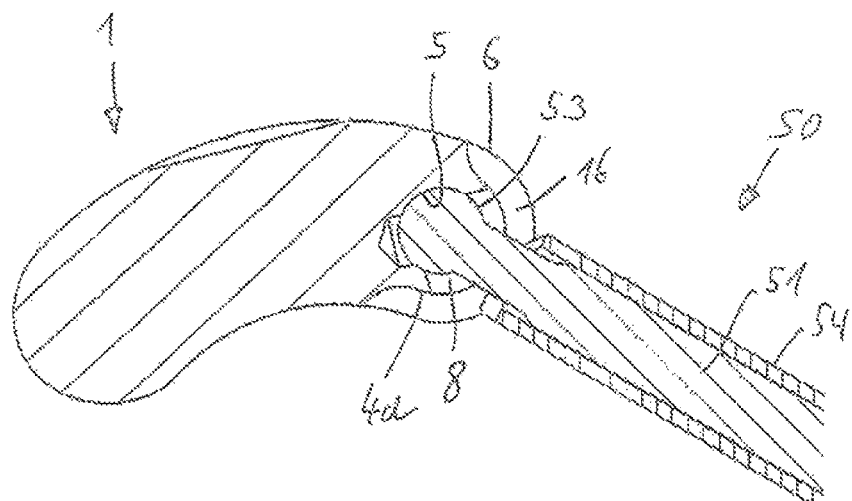
FIG. 5B shows the same as FIG. 5A, but in a cross-sectional top view.
Figure 6A:
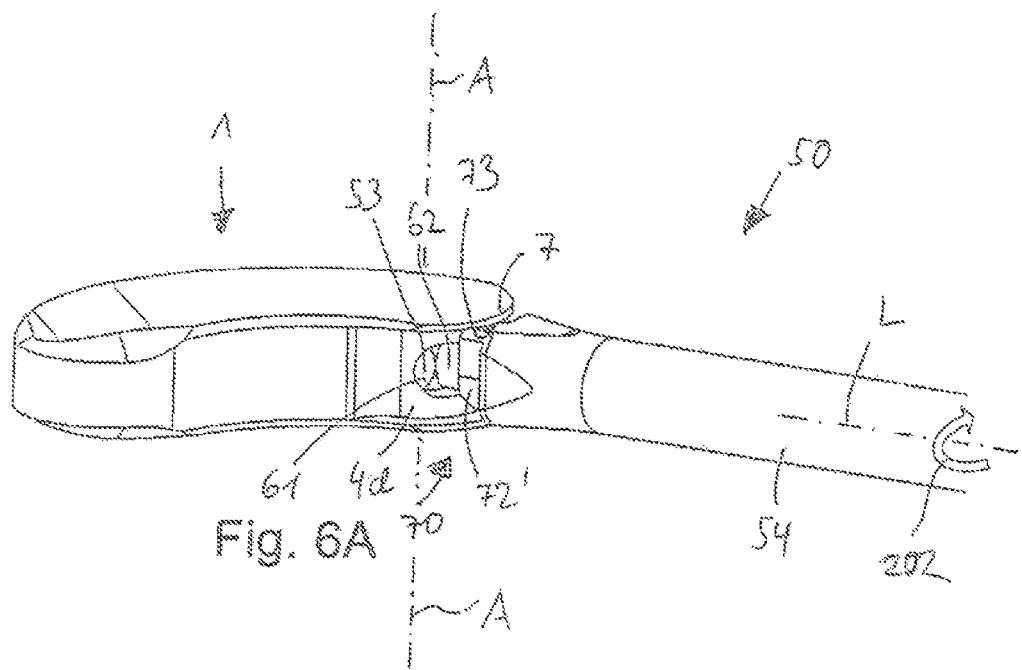
FIG. 6A shows the same as FIG. 5A, but after rotation of the drive shaft and engagement portion into a second state of a form-fit connection between the implant and the device.
Figure 6B:
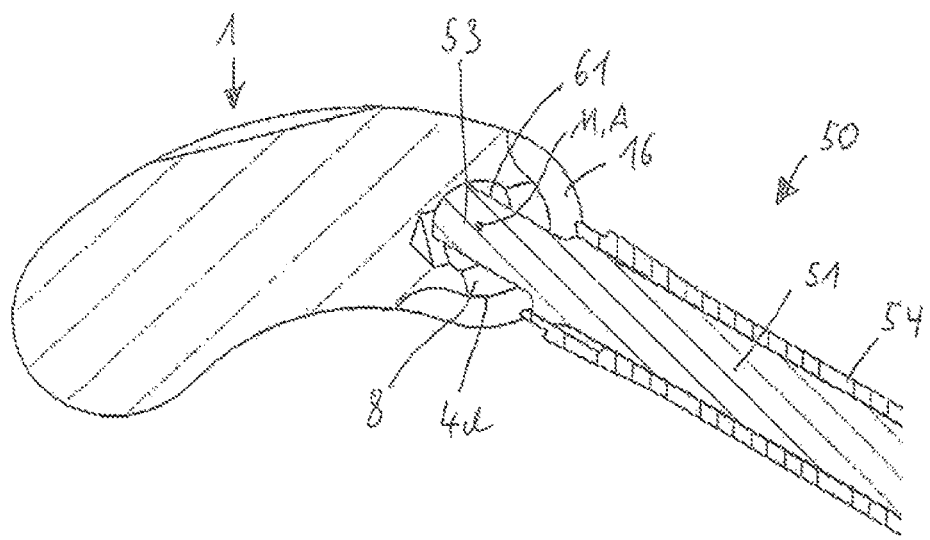
FIG. 6B shows the same as FIG. 6A, but in a cross-sectional top view.

FIGS. 5A and 5B depict a first state after performing a step of inserting (see arrow 101 in FIG. 5A) the engagement portion 53 of the drive shaft 51 through the elongate opening 8 into the hollow space 5 with the flat surfaces 61 of the engagement portion 53 being held in a horizontal posture (see FIG. 2A). In this first state, the engagement portion 53 and the neck portion 62 at the distal end of the drive shaft 51 project from the open distal end of the bore 65 of the sleeve 54 by a predetermined distance, such that when the engagement portion 53 abuts at the back surface of hollow space 5 in order to be fully received therein after insertion, the outer rounded guiding faces 72, 72' engage with the guiding surfaces 16, 17 of implant 1. In this posture, the stop faces 73, 73' only abut on the guiding surfaces 16, 17, respectively.

As a result, the guiding sleeve 54 can be rotated with respect to the guiding surfaces 16, 17 only in one direction, while the stop faces 73, 73', due to the abutment and larger diameter, impede rotation in the other direction.

FIGS. 6A and 6B depict a second state after performing a step of rotating (see arrow 102 in FIG. 6A) the guiding sleeve 54 along with the drive shaft 51 held therein by an angle α of 90° in the clockwise direction about the longitudinal axis L. The engagement portion 53 has now been brought into a form-fit connection with the hollow space 5 in view of the respective complementary shapes. The flat surfaces 61 of the engagement portion 53 are perpendicular to the elongate opening 8 and thus, the engagement portion 53 cannot be removed from the hollow space 5 in the rotated posture.

Also, while the rounded guiding faces 72, 72' allow sliding rotation of the sleeve 54 with respect to the guiding surfaces 16, 17, having rotated the sleeve 54 by about a quarter circle (i.e., α=90°), the stop faces 73, 73' again abut on the guiding surfaces 16, 17 to impede further rotation of the sleeve 54. This stop and end point of rotation provides the operator with a clear indication that a form-fit connection has been established. Also, in case that removal of the device 50 from the implant 1 is intended, for example when the implant 1 has been placed between two vertebrae, there is only one possibility of rotating back the sleeve 54 into the other direction (counterclockwise) by an angle α of 90°. This allows the operator to accurately control the handling of the device 50 and implant 1 under conditions of limited visibility.

Figure 7A:
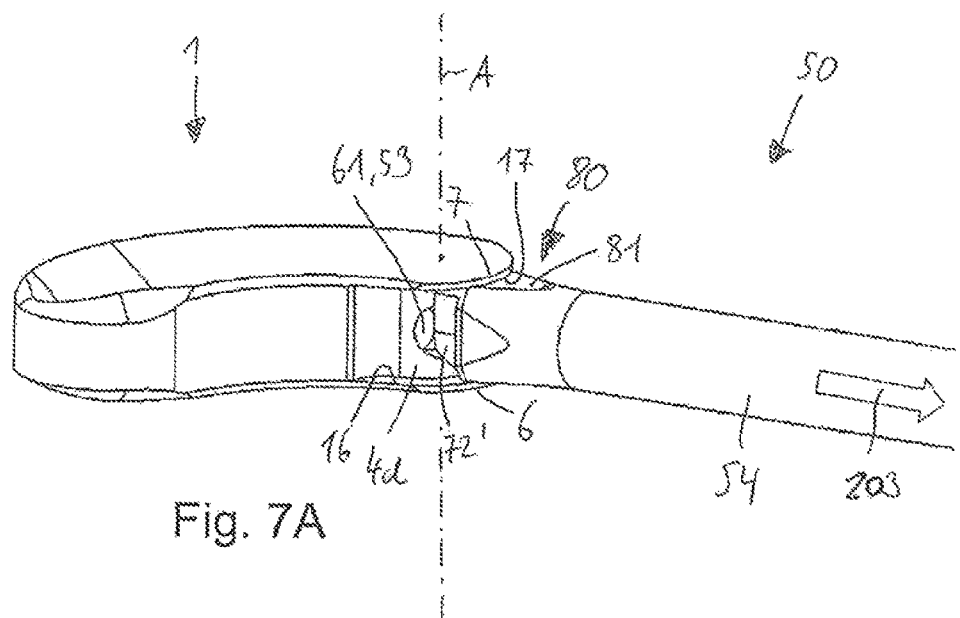
FIG. 7A shows the same as FIG. 6A, but after drawing back the drive shaft to lock the form-fit connection between the implant and the device in a third state.
Figure 7B:
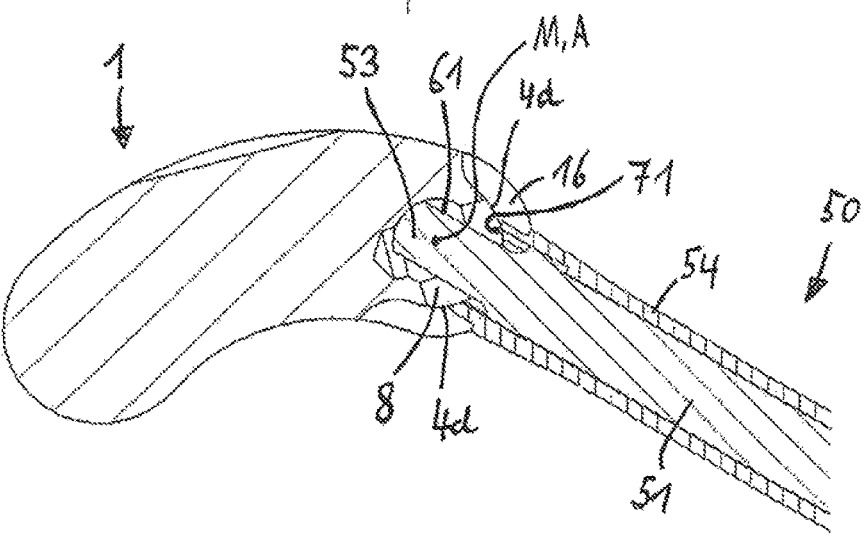
FIG. 7B shows the same as FIG. 7A, but in a cross-sectional top view.

FIGS. 7A and 7B depict a third state after performing a step of retracting the drive shaft 51 (see arrow 103) with respect to the guiding sleeve 54 by a predetermined distance using, for example, the adjustment nut 60 shown in FIG. 1. In this embodiment, the neck portion 62 is almost retracted within the bore 65 of the sleeve 54. Since the engagement portion 53 is firmly held in view of the form-fit connection with the hollow space 5, the sleeve 54 is thus drawn and moved toward the implant 1. More specifically, the front wall 71 of the first engagement structure 70 is brought in contact with the recessed portion 4d of the side wall 4 of the implant 1. Also, the rounded guiding faces 72, 72' and the abutment faces of the stops 73, 73' slide inwards at the guiding surfaces 16, 17.

As a result, flat faces 81 provided with respect to the second engagement structure 80, which are continuous with the abutment faces of the stops 73, 73' are brought into engagement with the guiding surfaces 16, 17 of the implant 1. However, since the second engagement structure 80 fails to have rounded guiding faces having a diameter equal to the distance between the guiding surfaces 16, 17, the guiding sleeve 54 can no more be rotated in this third state about its longitudinal axis L. Consequently, the form-fit connection between the engagement portion 53 and the hollow space 5 is locked or secured.

The knob 59 shown in FIG. 1 may be configured to interact with, for example, a protrusion or groove at the drive shaft 51 to provide a tactile response to the operator indicating that the drive shaft 51 has been retracted by a correct amount of distance such that the front wall may slide on the recessed portion 4d of the side wall 4 with less friction. Further retraction may serve to releasably fix a desired angular position between the device 50 and the implant 1, if necessary.

Figure 8A:
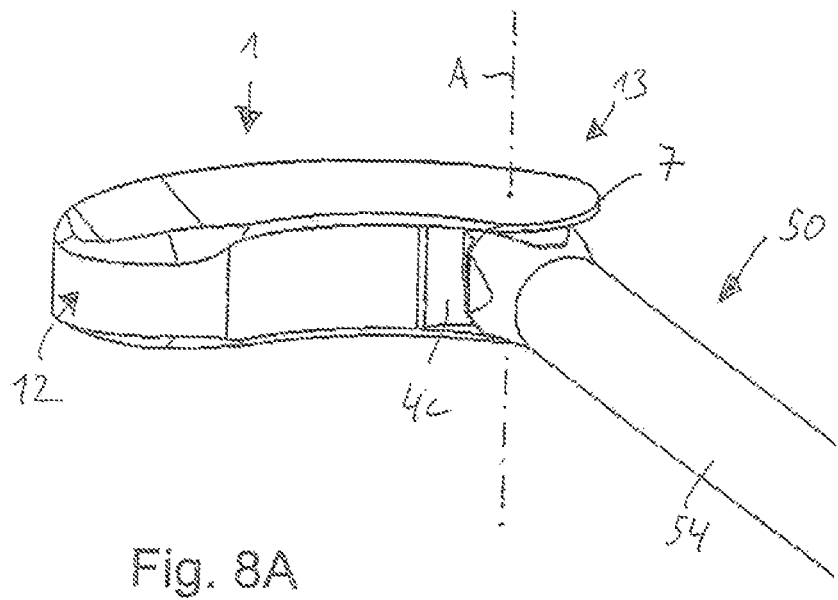
FIG. 8A shows in a perspective view the use of the intervertebral implant and the distal end portion of the device firmly connected as shown in FIG. 7A in a state wherein the implant is rotated up to a left side abutment between the drive shaft and the elongate opening.
Figure 8B:
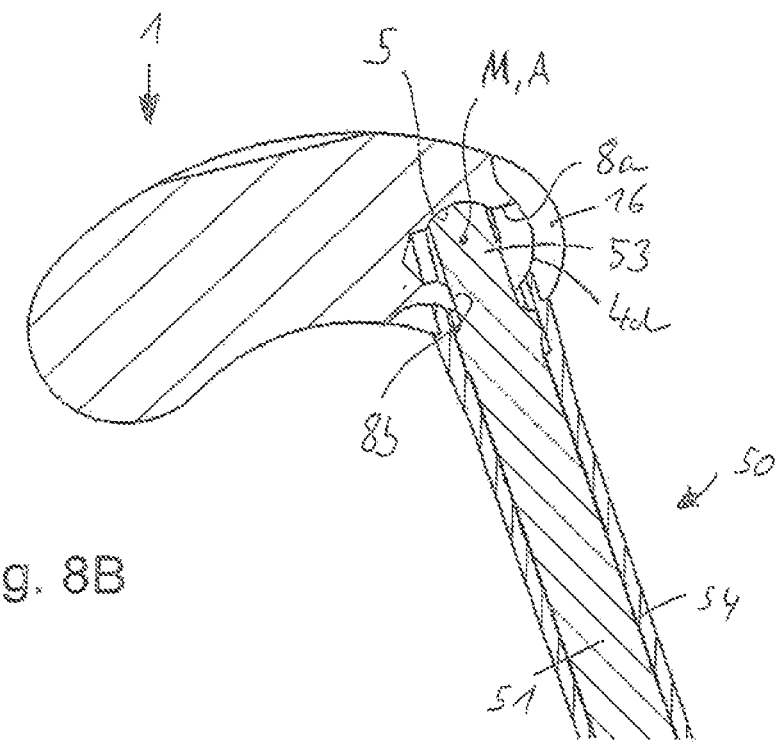
FIG. 8B shows the same as FIG. 8A, but in a cross-sectional top view.

FIGS. 8A and 8B depict a state of the implant 1 in which the angular position is changed from that shown in FIGS. 7A and 7B by sliding the engagement structures 70, 80 of the sleeve along the recessed portion 4d and the guiding surfaces 16, 17, respectively, leftward until a portion of the neck portion 62 still protruding from the sleeve 54 abuts on a left-side stop face 8b of the elongate opening 8.

Figure 9A:
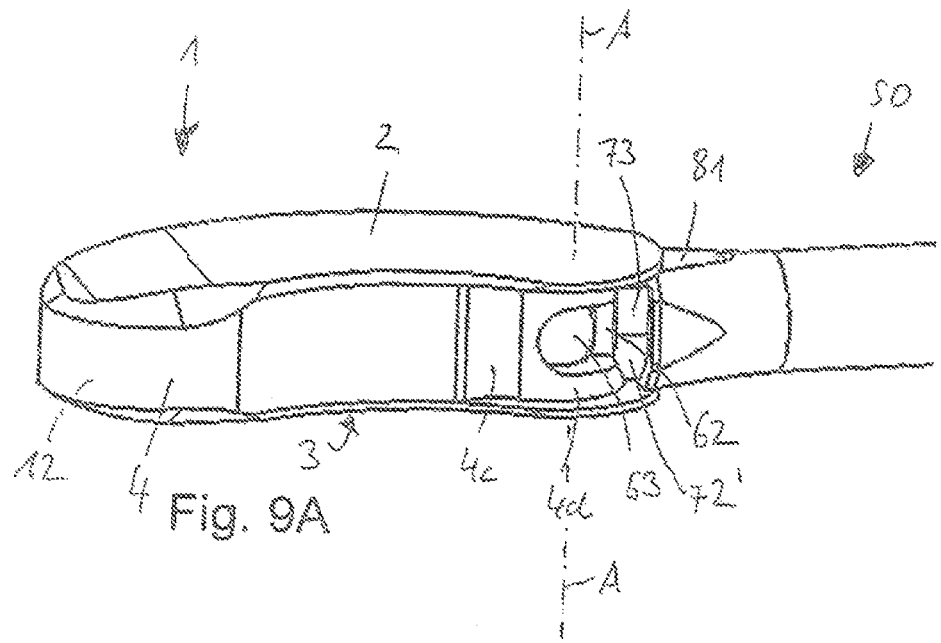
FIG. 9A shows in a perspective view the use of the intervertebral implant and the distal end portion of the device firmly connected as shown in FIG. 7A in a state wherein the implant is rotated up to a right side abutment between the drive shaft and the elongate opening.
Figure 9B:
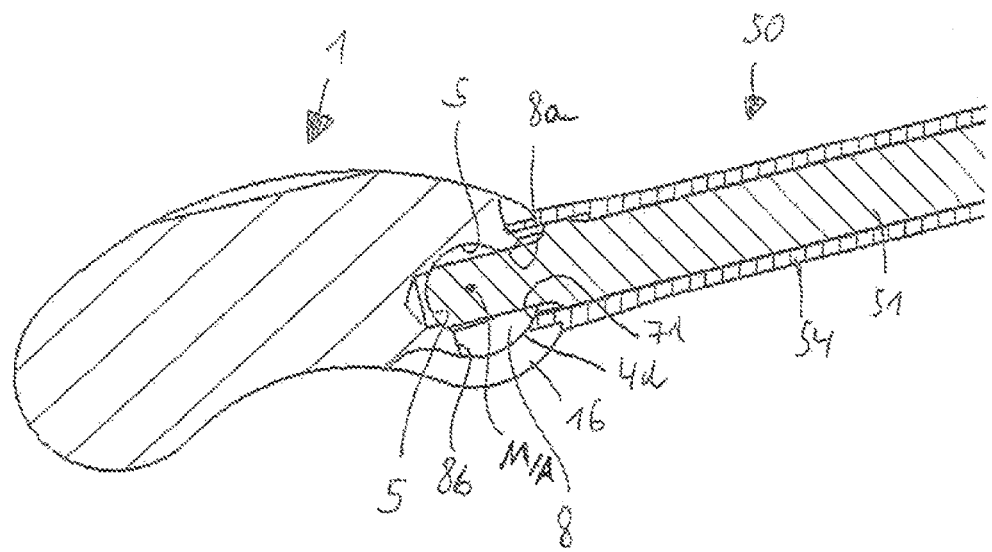
FIG. 9B shows the same as FIG. 9A, but in a cross-sectional top view.

Similarly, FIGS. 9A and 9B depict a state of the implant 1 in which the angular position is changed from that shown in FIGS. 7A and 7B by sliding the engagement structures 70, 80 of the sleeve along the recessed portion 4d and the guiding surfaces 16, 17, respectively, rightward until a portion of the neck portion 62 still protruding from the sleeve 54 abuts on a right-side stop face 8a of the elongate opening 8.

Using the steps as outlined above, a placement of the implant 1 according to the embodiment between two vertebrae may be performed using the device 50 for inserting the implant in a method as illustrated, for example, in FIGS. 9a) through 9f) of document EP 2 535 022 A1, which is in this regard Incorporated herein by reference, wherein implant 1 and device 20 of that document are replaced with the implant 1 and the device 50 of the present embodiment.

Figure 10:
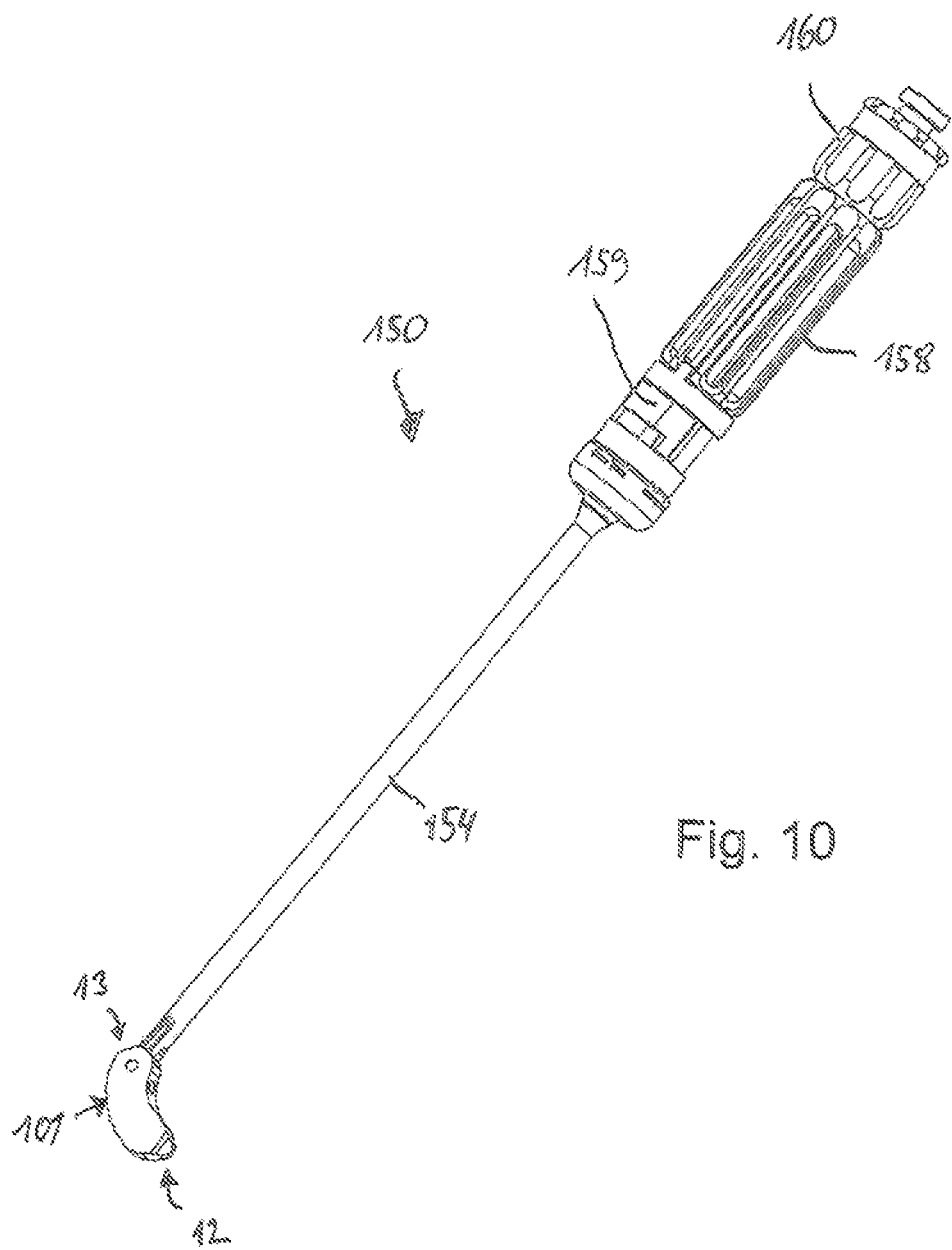
FIG. 10 shows in a perspective view an overview of an intervertebral implant held by a device for inserting the implant into a body according to second embodiments of the invention.

Next, second embodiments both of an intervertebral implant as well as of a device, respectively, for inserting an intervertebral implant into a body are explained with reference to FIGS. 10-18B. The overall structure of the implant of this second embodiment is similar to that of the first embodiment and repeated discussion of similar features will be omitted in the following. One difference between the embodiments of the system can be seen in that only a first engagement structure 180 is provided at the device in the second embodiment, but a second engagement structure is omitted herein. In the first embodiment, the engagement structure 70 allows for a joint rotation of the guiding sleeve and the drive shaft with respect to the implant in order to establish the form-fit connection. In the second embodiment, as will be described below, a rotation of the drive shaft with respect to the guiding sleeve is allowed such that a more simple sleeve design may be provided. FIG. 10 shows in a perspective view an overview of an intervertebral implant 101 held by such a device 150 for inserting the implant into a space between two vertebrae of the vertebral column.

The device 150 comprises a drive shaft 151 (see FIGS. 11A, 11B), a guiding sleeve 154, a handle 158, a turning handle 159 and an adjusting means 160, which may be an adjusting nut similar to the adjusting means 60 of the first embodiment, and which similarly interacts with the drive shaft 151 via threads. The drive shaft 151 is movably guided within the sleeve 154 and can be advanced or retracted with respect to the sleeve 154 by actuating the adjusting means 160. Other means to facilitate advancement or retraction of the drive shaft 151 with respect to the guiding sleeve 154 may be contemplated as well, and the invention is not limited to a specific embodiment. The turning handle 159 permits rotation of the drive shaft 151 with respect to the guiding sleeve 154.

FIGS. 12A through 12E show details of the distal end of drive shaft 151. The drive shaft 151 comprises an engagement portion 153 having a spherical segment-shaped surface 157, wherein flat or planar surfaces 161, 161' are provided on opposite sides thereof as in the first embodiment. Position marks 269 are provided on one or both of the flat surfaces 161, 161' in the form of a strip. The strip indicates to the operator an orientation of the engagement portion 153 within the hollow space as will be explained below.

The engagement portion 153 is also connected to a main portion 163 of the drive shaft 151 via a neck portion 162, which has a diameter smaller than a diameter of the main portion 163 as well as of the engagement portion 153, when the spherical segment-shaped surface 157 is considered, similar to the first embodiment. However, the diameter of the neck portion 162 is substantially the same as the width of the engagement portion 153 in a direction perpendicular to the opposite flat surfaces 161, 161', as can directly be seen in FIG. 12B. The main portion 163 has a cylindrical shape which in this embodiment allows the drive shaft 151 to be rotated with respect to the guiding sleeve 154.

Similar to the first embodiment, the intervertebral implant 101 of the second embodiment is also substantially of a kidney shape including a leading end 12 and a trailing end 13, a top surface 102, a bottom surface 103, and a side wall 104 extending between the top and bottom surfaces 102, 103. The top and bottom surfaces 102, 103 are substantially planar and parallel to each other except an inclined portion 102a, which extends towards the leading end 12.

Figure 11A:
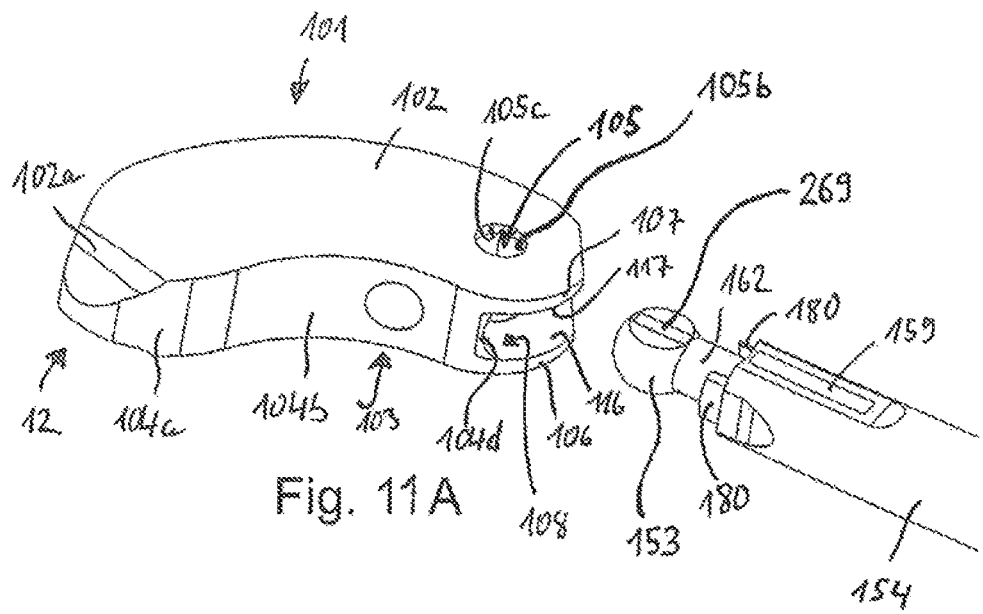
FIG. 11A shows an enlarged perspective view of the intervertebral implant and a distal end portion of the device as shown in FIG. 10 in a state prior to insertion.

The sidewall 104 has a rounded portion 104a at the leading end 12, a concave portion 104b on a lateral side, a recessed portion 104d formed by inwardly extending wall portions at the trailing end 13 which will be explained in more detail below, and a convex portion 104e on the opposite lateral side The top surface 102 as well as the bottom surface 103 each form an edge with each of the portions 104a, 104b and 104e of the side wall 104 at the leading end 12 and the lateral sides of the implant 101. At the trailing end 13, the top surface 102 extends beyond the inwardly extending wall portions which form the recessed portion 104d of the side wall 104. As a result, overhanging extensions 106, 107 are formed as shown in FIG. 11A. An outer contour of the implant 101 may be defined by the edges of the top and bottom surfaces 102 and 103 in this example including the edges of the extensions 106 and 107.

Substantially planar surfaces 116, 117 are provided by these extensions 106 and 107, respectively, due to the presence of the recessed portion 104d of the side wall 104. The surfaces 116, 117 extend along or around the trailing end 13 in an arc-shaped manner and face towards each other with the recessed portion 104d extending therebetween. Thus, a recess is formed in the outer contour at the trailing end 13 of the implant 101, which is limited by the recessed portion 104d of the side wall 104 and the surfaces 116, 117 of the extensions 106, 107. As in the first embodiment, the surfaces 116, 117 may be denoted as guiding surfaces. In an embodiment, the guiding surfaces 116, 117 of the second embodiment are parallel to each other, but may also be inclined or rounded.

Figure 11B:
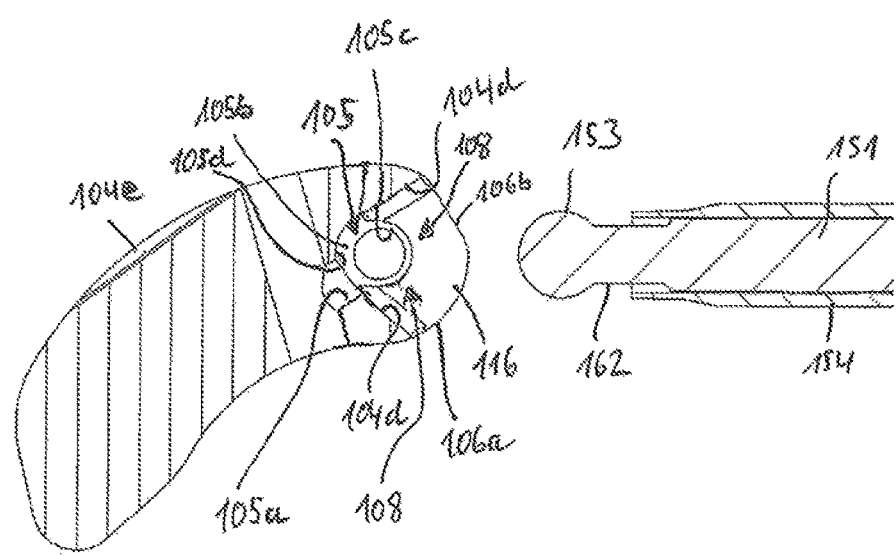
FIG. 11B shows the same as FIG. 11A, but in a cross-sectional top view.

A hollow space 105 is provided within the implant 101 as can best be seen in FIGS. 11A and 11B and has a shape of a sphere or spherical segment. The hollow space 105 of the second embodiment is formed by each of spherical segments 105b provided within extensions 106, 107 and facing each other, and by a spherical wall portion 105d which is in this example continuous with the inwardly extending wall portions of the recessed portion 4d. The hollow space 105 is open towards the outside. The inwardly extending wall portions of the recessed portion 104d form an elongate opening 108, which thus extends through the recessed portion 104d and provides access to the hollow space 105. The elongate opening 108 has a horizontal length larger than its vertical height and extends across the recessed portion 104d between respective wall portions provided as right side stops and left side stops along a direction substantially parallel to the plane of the top and bottom surfaces 102 and 103.

The hollow space 105 has a diameter which is larger than the vertical height of the elongate opening 108, i.e., larger than a distance between the guiding surfaces 116, 117. In this embodiment, the diameter is sufficiently large such that a circular hole 105c is created in each of the top surface 102 and the bottom surface 103. The circular holes 105c allow an operator to inspect an orientation of the engagement portions 153 of the drive shaft 151 when being received in the hollow space 105. The diameter of the hollow space 105 is the same or slightly larger than a diameter of the engagement portion 153 to permit receiving, rotating and supporting the engagement portion 153 therein. Further, in this embodiment, a distance between the guiding surfaces 116, 117 is the same as or slightly larger than a distance between the flat or planar surfaces 161, 161' of the engagement portion 153 to allow insertion of the engagement portion 153 into the elongate opening 108 in a horizontal posture. The hollow space 105 may be manufactured as in the first embodiment, for example by furnishing a cylindrical core bore hole 105a first, etc.

Moreover, the hollow space 105 has a symmetrical center point M defined by the spherical segment-shaped surfaces 105b, 105d. Further, the guiding surfaces 116, 117 are concentric about an axis A extending through the center point M, which extends vertically (perpendicular to the plane of surfaces 102, 103) through the implant. Axis A represents a rotation axis of the implant 101 with respect to the device 150. The guiding surfaces 116, 117 are engaged by an engagement structure 180 provided at a distal end face of the guiding sleeve 154 when a connection is established between the device 150 and the implant 101 as shown in FIG. 10. Also, when the engagement portion 153 is supported in the hollow space 105, the neck portion 162 having the diameter which is the same as the distance between the flat or planar surfaces 161, 161' of the engagement portion 153 is thus also sandwiched and slideably guided between the guiding surfaces 116, 117 which further increases the stability and robustness of the system during engagement.

The guiding sleeve 154 and the engagement structure 180 are explained with reference to FIGS. 13A through 13E. As can be seen, the sleeve 154 is provided with a first engagement structure 180 in the form of two projections 180a having a cylindrical-segment-shape and extending in a distal direction from the distal end face. The distal end face has a substantially annular shape and comprises a concave portion 171a and a planar portion 171b. The two projections 180a each extend from the planar portion 171b and are located diametrically opposite to each other. An inner wall of each of the projections 180a is continuous with a surface of an inner bore 165 of the sleeve 154. Thus the two projections 180a also extend in a circumferential direction around the inner bore 165 between respective end faces thereof. These end faces in this embodiment have a planar shape and are parallel to each other. These end faces form guiding faces 181 configured for sliding engagement with the guiding surfaces 116, 117 of the implant. The distance between each two guiding faces 181 of one projection 180a is the same or slightly less than a distance between the guiding surfaces 116, 117 of the implant 101. As a result. In an attached state of the device 150 and the implant 101 the projections 180a are sandwiched between the guiding surfaces 116, 117 with the guiding faces 181 being in sliding engagement.

The concave portion 171a is positioned between the projections 180a in a circumferential direction and has a curvature which corresponds to that of the arc shaped outer contour of extensions 106, 107 to allow sliding and/or tight locking upon actuation of the adjusting means 160. It is noted that according to further modifications, the portions 171a may also be planar. Further, the guiding faces 181 may also have rounded shape and may be inclined with respect to each other and with respect to the guiding surfaces of the implant when the device is attached. Further, the sleeve 154 may have a flattened portion 257 extending from the concave portion 171a of the distal end face along an outer surface of the sleeve and a portion 258 extending from the planar portion 171b in a similar manner. The flattened portions facilitate gripping (portion 157) or receiving a position mark 259 provided as a strip.

Operation of the device 150 and implant 101 is explained with reference to FIGS. 14A through 18B. Different from the first embodiment, upon inserting the drive shaft 151 into the implant 101 according to the second embodiment, the first engagement structure 180 engages with the guiding surfaces 116, 117 in all states of the attachment process, i.e., in a first state of insertion of the engagement portion 153 into the hollow space 105 illustrated in FIGS. 14A and 14B, in a second state wherein a form-fit connection has been established as illustrated in FIGS. 15A and 15B, and in a third state wherein a connection is locked by drawing back the drive shaft 151 supporting the implant and thereby pressing the concave portion 171a of the sleeve 154 in the opposite direction against the outer contour of the extensions 106, 107.

Figure 14A:
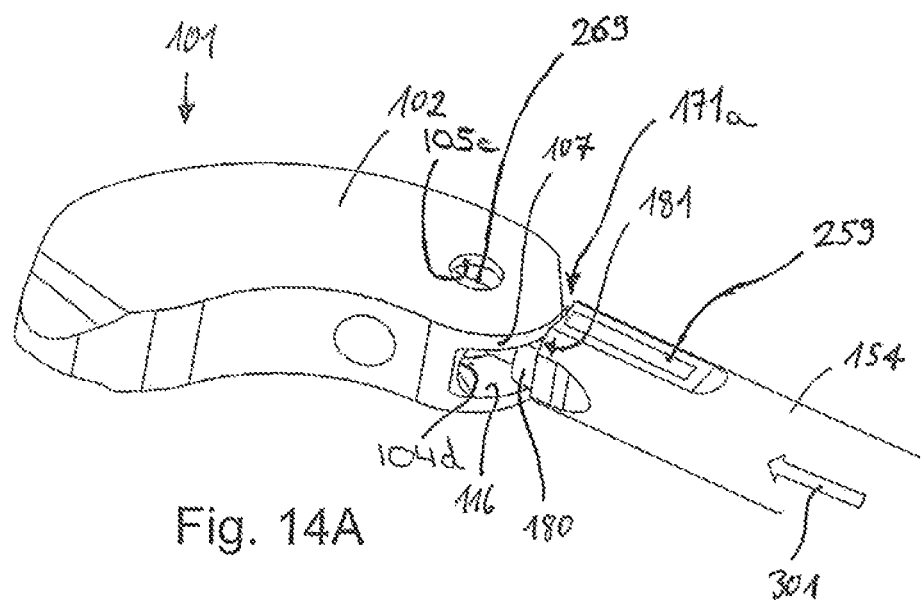
FIG. 14A shows the same as FIG. 11A, but in a first state of insertion of the drive shaft and engagement portion into the intervertebral implant.
Figure 14B:
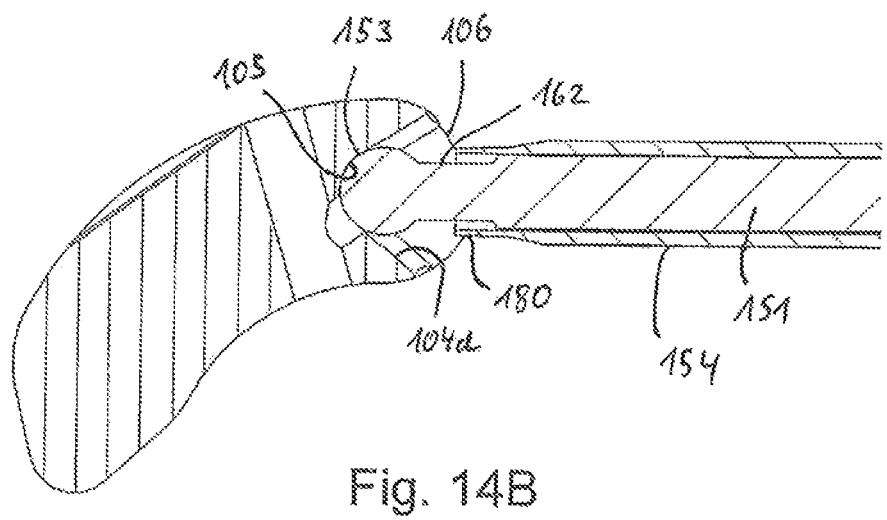
FIG. 14B shows the same as FIG. 14A, but in a cross-sectional top view.

More specifically, FIGS. 14A and 14B depict a first state after performing a step of inserting (see arrow 301 in FIG. 14A) the engagement portion 153 of the drive shaft 151 through the elongate opening 108 into the hollow space 105. As in the first embodiment the flat surfaces 161 of the engagement portion 153 are held in a horizontal posture (FIG. 11A or 12A). Thereby, the engagement portion 153 and the neck portion 162 at the distal end of the drive shaft 151 project from the open distal end of the inner bore 165 of the sleeve 154 by a predetermined distance, such that when the engagement portion 153 abuts at the back surface of the hollow space 105, the projections 180a of engagement structure 180 enter the channel or elongate opening 108. As a result, the guiding faces 181 at the projections 180a engage with the guiding surfaces 116, 117 of implant 101. Also, the arrangement of the two guiding faces 181 on either side of the sleeve 154 prevents any rotation of the sleeve 154 around its longitudinal direction L. Moreover, the concave portions 171a of the distal end surface of the guiding sleeve 154 abut on the arc-shaped outer contour of the implant 101 in a region of the extensions 106, 107, which includes the corresponding curvature. In this posture shown in FIG. 14A, the position mark 269 of the drive shaft 151 is still aligned (see FIG. 11A) with the position mark 259 at the sleeve, and is visible through the circular hole 105c.

Figure 15A:
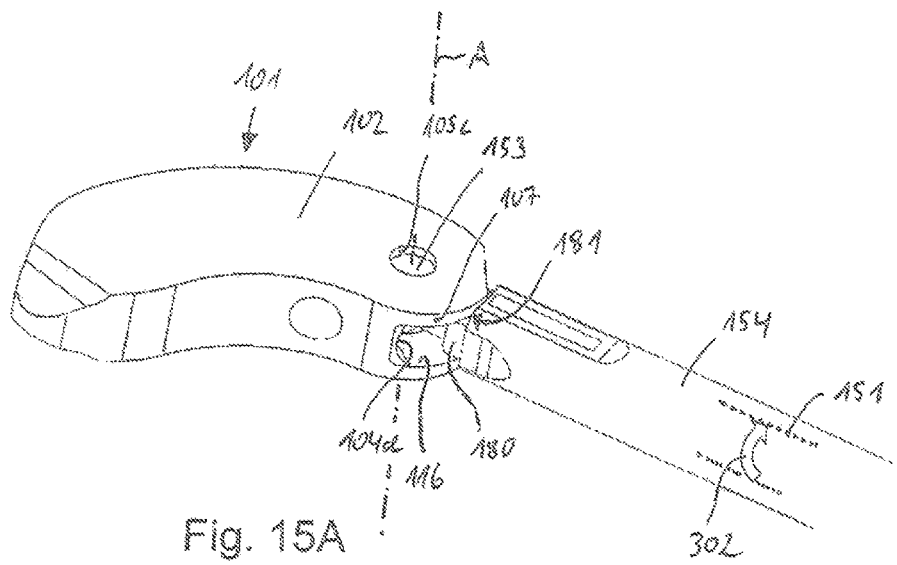
FIG. 15A shows the same as FIG. 14A, but after rotation of the drive shaft and engagement portion into a second state of a form-fit connection between the implant and the device.
Figure 15B:
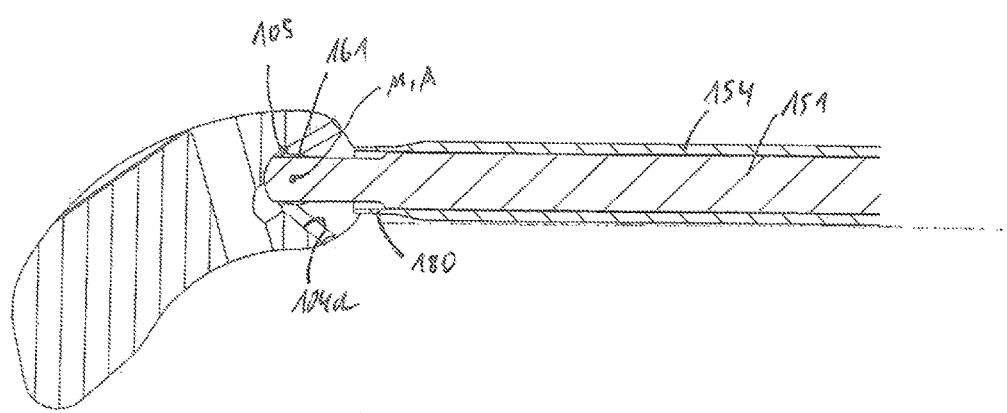
FIG. 15B shows the same as FIG. 15A, but in a cross-sectional top view.

FIGS. 15A and 15B depict a second state after performing a step of rotating the drive shaft 151 (see arrow 302 in FIG. 15A, the drive shaft is indicated with dotted lines) by an angle α of 90° in the clockwise direction about the longitudinal axis L with respect to the guiding sleeve 154. This rotation may be effected by actuating the turning handle 159 provided at the handle 158 as shown in FIG. 10. The engagement portion 153 is thereby transferred into a form-fit connection with the hollow space 105. Like in the first embodiment, the engagement portion 153 cannot be removed from the hollow space 105 in the rotated posture. Meanwhile, the position mark 269 disappeared from the circular hole 105c due to the rotation of the drive shaft 151.

Figure 16A:
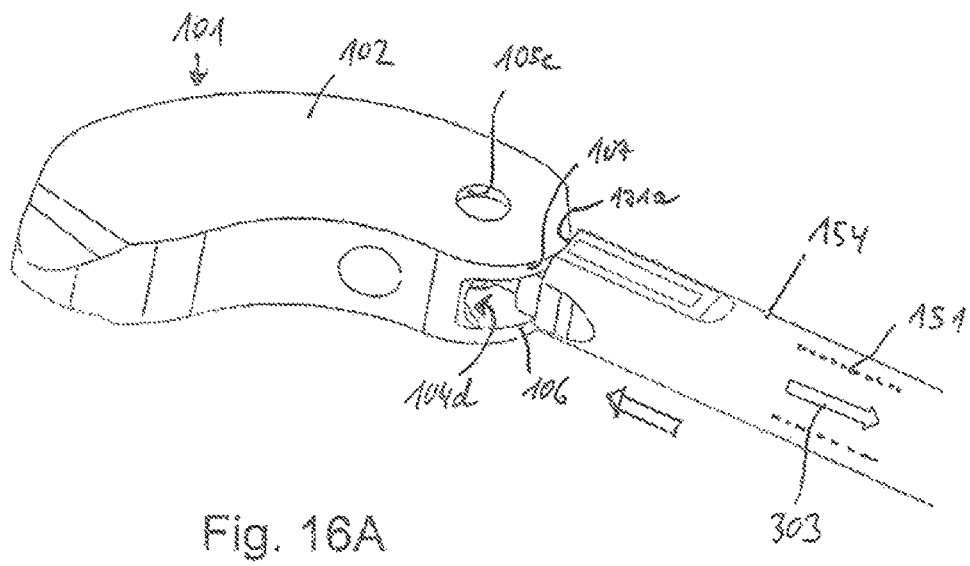
FIG. 16A shows the same as FIG. 15A, but after drawing back the drive shaft to lock the form-fit connection between the implant and the device in a third state.
Figure 16B:
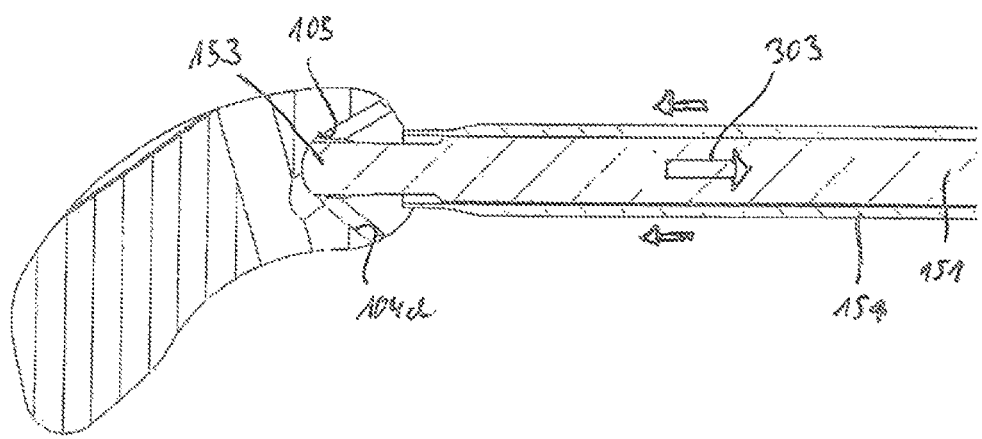
FIG. 16B shows the same as FIG. 18A, but in a cross-sectional top view.

FIGS. 16A and 16B depict a third state after performing a step of drawing back the drive shaft 151 (see arrow 303) with respect to the guiding sleeve 154 using, for example, the adjustment nut 160 shown in FIG. 10. Thereby, the sleeve 154 is urged in the distal direction and pressed via concave portion 171a against the outer contour of the extensions 106, 107, while the drive shaft 151 is drawn back into the proximal direction with the implant 101 held in the form-fit connection. Unlike the first embodiment, the mutual displacement between the drive shaft 151 and the guiding sleeve 154 is small, and no further engagement portion is introduced into the channel of the implant 101 between the guiding surfaces 116 and 117. The instant step of drawing back the drive shaft 151 with respect to the sleeve 154 thus only serves to fix or lock an angular position of the implant 101 with respect to the device 151, or to adjust the amount of friction between the guiding faces and surfaces.

Figure 17A:
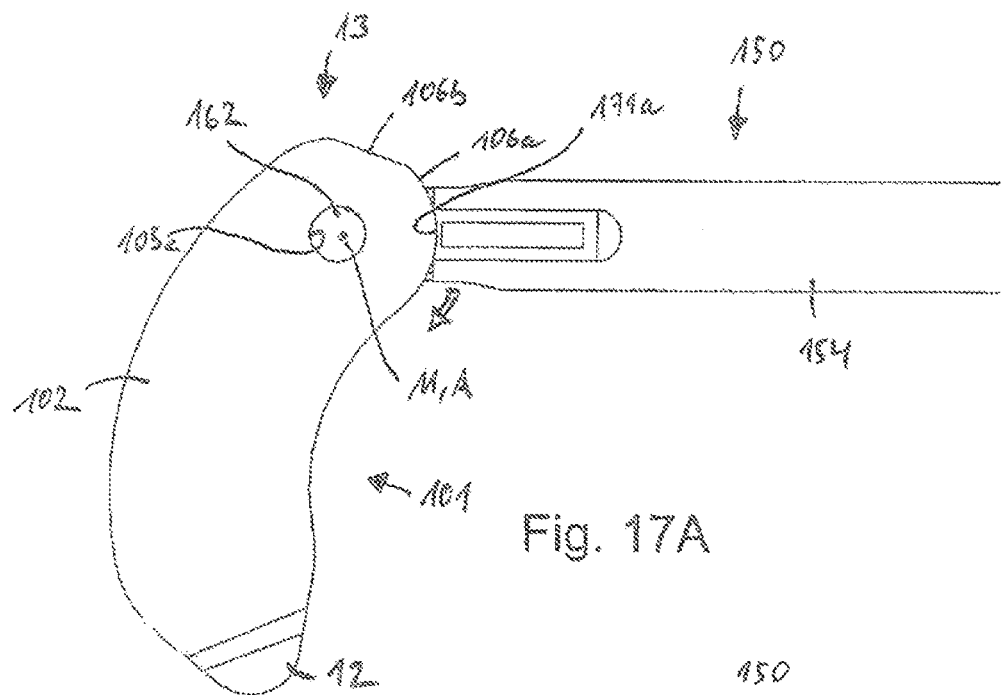
FIG. 17A shows in a top view the use of the intervertebral implant and the distal end portion of the device firmly connected as shown in FIG. 16A in a state wherein the implant is rotated up to a left side abutment between the drive shaft and the elongate opening.
Figure 17B:
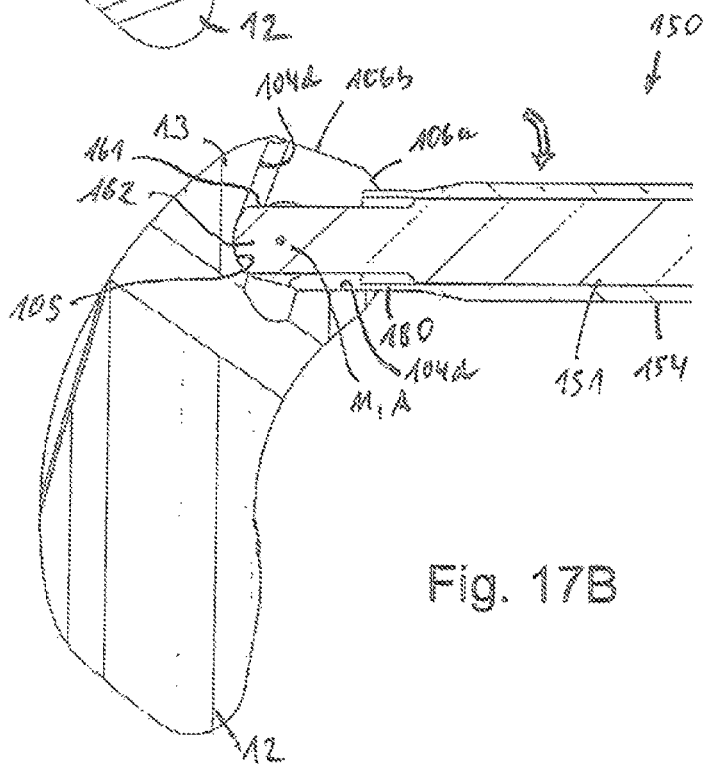
FIG. 17B shows the same as FIG. 17A, but in a cross-sectional top view.

FIGS. 17A and 17B depict a state of the implant 101 in which the angular position is changed from that shown in FIGS. 16A and 16B by sliding the engagement structure 180 of the guiding sleeve along the outer contour of the extensions 106, 107 and the guiding surfaces 116, 117, leftward (indicated by the arrows) until one of the projections 180a of the sleeve 154 abuts on a left-side inwardly extending wall portion of the recessed portion 104d, or elongate opening 108, respectively. The rotation of the implant 101 is around axis A extending through the center point M of the hollow space 105. Herein, the concave portion 171a of the distal end face of the sleeve 154 abuts against and slides with respect to the arc-shaped or curved portion 106a of the outer contour of extensions 106, 107. The curvatures correspond to each other such that a smoothly guided sliding contact at a constant radial distance from center point M of the hollow space 105 is achieved.

Figure 18A:
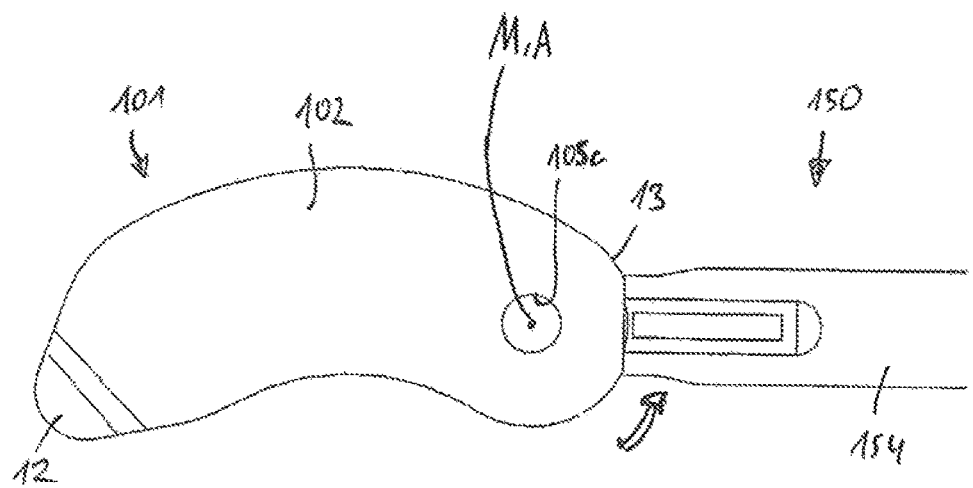
FIG. 18A shows in a top view the use of the intervertebral implant and the distal end portion of the device firmly connected as shown in FIG. 16A in a state wherein the implant is rotated up to a right side abutment between the drive shaft and the elongate opening.
Figure 18B:
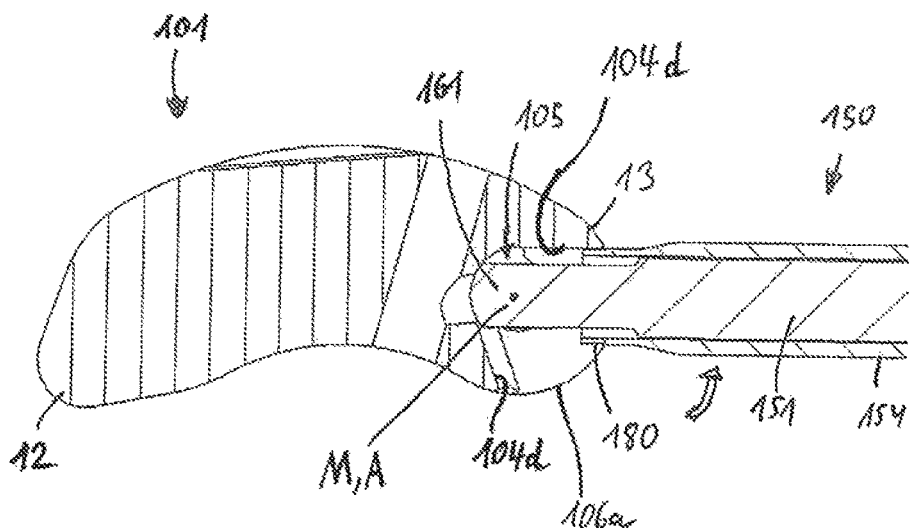
FIG. 18B shows the same as FIG. 18A, but in a cross-sectional top view.

Similarly, FIGS. 18A and 18B depict a state of the implant 101 in which the angular position is changed from that shown in FIGS. 16A and 16B by sliding the engagement structure 180 of the guiding sleeve 154 along the outer contour of the extensions 106, 107 and the guiding surfaces 116, 117 rightward (see arrows in FIGS. 18A, 18B) until the other one of the projections 180a of the sleeve 154 abuts on a right-side inwardly extending wall portion of the recessed portion 104d, or elongate opening 108, respectively. As noted above, the rotation of the implant 101 is around axis A. Herein, the planar portion 171b of the distal end face of the guiding sleeve 154 abuts against and slides with respect to the correspondingly shaped straight portion 106b of the outer contour of extensions 106, 107 which is recessed from curved portion 106a with regard to a radial distance from the center point M. If a slight pressure force exerted on the sleeve in a distal direction is maintained throughout rotation of the implant 101 around axis A, the sleeve thus latches-in, when reaching the position shown in FIGS. 18A and 18B. The latched-in state provides for a particular robust connection between the implant and the device during transfer to the implant site.

Various modifications of the implant and/or the device may be made without departing from the scope of the invention as defined in the appended claims.

Namely, the implant shown in the above described embodiment is only an example. The contour and shape of the implant may be different according to the specific clinical requirements. For example, the contour may have any other shape, such as circular, rectangular, oval, etc. In some embodiments, the height of the side wall may be constant throughout the implant.

Moreover, the elongate opening can be at another position. Still further, the elongate opening may extend vertically or in an inclined posture. Also, only one opening or more than one opening may be provided. Also, it may be possible to adapt existing intervertebral implants without an opening, by providing it with such an opening as proposed herein.

According to further modifications, the recessed portions 4c and/or 4d of the side wall 4, and/or the front wall 71 of the sleeve 54, may be provided with ratcheting features, or teeth or ribs and grooves, or roughened surfaces to increase a clamping force, when brought into contact with each other. Alternatively, the surface may be coated to increase friction.

In the above embodiments, the drive shaft 51 may be rotated by an angle α of about 90°. However, other ranges of rotation are possible as well. Also, when the respective stops 73, 73' having abutment faces are provided to define end points of rotation, releasable snap-in means may be provided to provide a tactile response to the operator, that a desired state has been reached with respect to the engagement portion 53.

Similarly, when the second embodiment is concerned, stops defining end points may be provided with regard to the rotation of the drive shaft within the sleeve.

The implant is made of a biocompatible material. For example, the implant can be made of stainless steel or titanium, or of a biocompatible metal alloy, such as a nickel titanium alloy, for example Nitinol, or can be made of a biocompatible plastic material, for example, PEEK (polyetheretherketone).

Alternative aspects of the invention may also be contemplated, wherein the portion of the side wall, which includes the elongate opening, may not be recessed or set back from an outer contour.

In one or more embodiments, an intervertebral Implant having the hollow space 5 formed within the implant and accessible through the elongate opening 8 extending through the recessed portion 4d of the side wall 4 is provided, wherein the hollow space 5 is shaped to receive the engagement portion 53 of the drive shaft 51 of the device 50 for insertion of an implant; wherein the hollow space 5 is shaped to receive the engagement portion 53 of the drive shaft 51 of the insertion tool 50 in a first state of insertion, and to support the engagement portion 53 in a second state in a form-fit connection, in which the engagement portion 53 is rotated from the first state by an angle α. The hollow space may have a spherical shape.

In a specific aspect, an intervertebral implant having the hollow space 5 formed within the Implant and accessible through the elongate opening 8 extending through the recessed portion 4d of the side wall 4 is provided, wherein the hollow space 5 is shaped to receive the engagement portion 53 of the drive shaft 51 of the device 50 for insertion of an implant; wherein the hollow space 5 has a spherical shape.

Alternative aspects of the invention may also be contemplated, wherein the first engagement structure or the second engagement structure is omitted, respectively, and only one of the engagement structures is implemented, while the other features may be the same as defined in the appended claims.

The invention claimed is:

1. A system comprising an intervertebral implant and a device to insert the intervertebral implant into a body, the intervertebral implant comprising a top surface, a bottom surface, and a side wall extending between the top surface and the bottom surface, the intervertebral implant having a hollow space having a spherical segment shape formed within the intervertebral implant and accessible through an elongate opening extending through a recessed portion of the side wall, and at least two guiding surfaces extending along an end of the intervertebral implant in an arc-shaped manner and facing one another such that the recessed portion of the side wall extends therebetween, wherein the device comprises:
    a drive shaft including an engagement portion configured to engage the intervertebral implant in the hollow space; and
    a sleeve movably holding and guiding the drive shaft and having a longitudinal axis, wherein the sleeve comprises an engagement structures;
    wherein when the engagement portion of the drive shaft is received in the hollow space through the elongate opening and rotated by an angle about the longitudinal axis such that the engagement portion is supported in the hollow space, the engagement structure of the sleeve is configured to engage and slide laterally along the arc-shape of the at least two guiding surfaces, while being shaped to prevent rotation of the sleeve relative to the at least two guiding surfaces about the longitudinal axis.

2. The system according to claim 1, wherein the recessed portion is set back from an outer contour of the intervertebral implant such as to provide the at least two guiding surfaces.

3. The system according to claim 1, wherein at the location of the recessed portion of the side wall, an outer contour of the intervertebral implant is provided by an extension of the top surface and an extension of the bottom surface, each extending beyond the recessed portion of the side wall.

4. The system according to claim 3, wherein the hollow space has a center point, wherein each of the extensions comprises a respective one of the at least two guiding surfaces, wherein each of the at least two guiding surfaces is concentric about a longitudinal axis extending through the center point.

5. The system according to claim 1, wherein the intervertebral implant is a transforaminal lumbar interbody fusion (TLIF) implant having a kidney-shape, and includes a leading end and a trailing end, and wherein the hollow space, the recessed portion of the side wall, and the elongate opening are provided at or adjacent the trailing end.

6. The system according to claim 1, further comprising an adjusting device configured to adjust a position of the drive shaft with respect to the sleeve along the longitudinal axis.

7. The system according to claim 1, further comprising a resilient knob cooperating with the drive shaft and being indicative of a position of the drive shaft with respect to the sleeve along the longitudinal axis, in which the engagement structure engages the at least two guiding surfaces.

8. The system according to claim 1, wherein the hollow space has a center point, wherein the recessed portion of the side wall is arranged to be concentric about a longitudinal axis extending through the center point.

9. The system according to claim 8, wherein the recessed portion of the side wall has a cylindrical shape or a spherical shape.

10. The system according to claim 1, wherein the sleeve further comprises another engagement structure adjacent the engagement structure and including a guiding face configured to engage one of the at least two guiding surfaces, wherein the guiding face has a rotational symmetry about the longitudinal axis of the sleeve to allow rotation of the sleeve with respect to the one of the at least two guiding surfaces.

11. The system according to claim 10, wherein the another engagement structure includes at least one stop configured to limit a rotation of the sleeve with respect to the at least two guiding surfaces, to each define only one direction of rotation for transferring the engagement portion of the device from a first state into a second state and vice versa, respectively.

12. The system according to claim 1, wherein the drive shaft and the sleeve each comprises a guiding structure configured to limit a movement of the drive shaft to that in a direction along the longitudinal axis, but prevent a rotation of the drive shaft with respect to the sleeve.

13. A system comprising an intervertebral implant and a device to insert the intervertebral implant into a body, the intervertebral implant comprising a top surface, a bottom surface, and a side wall extending between the top surface and the bottom surface, the intervertebral implant having a hollow space having a spherical segment shape formed within the intervertebral implant and accessible through an elongate opening extending through the side wall at an end of the intervertebral implant, the intervertebral implant further comprising at least two guiding surfaces extending along the end of the intervertebral implant in an arc-shaped manner and facing one another, wherein the device comprises:

a drive shaft including an engagement portion configured to engage the intervertebral implant in the hollow space; and a sleeve movably holding and guiding the drive shaft and having a longitudinal axis, wherein the sleeve comprises an engagement structures;

wherein when the engagement portion of the drive shaft is received in the hollow space through the elongate opening and rotated by an angle about the longitudinal axis such that the engagement portion is supported in the hollow space, the engagement structure of the sleeve is configured to engage and slide laterally along the arc-shape of the at least two guiding surfaces, while being shaped to prevent rotation of the sleeve relative to the at least two guiding surfaces about the longitudinal axis.

14. The system according to claim 13, wherein at a location of the side wall at the end of the intervertebral implant, an outer contour of the intervertebral implant is provided by an extension of the top surface and an extension of the bottom surface, each of the extensions comprising a respective one of the at least two guiding surfaces.

15. The system according to claim 14, wherein the hollow space has a center point, and the outer contour at each of the extensions is concentric about a longitudinal axis extending through the center point.

16. The system according to claim 14, wherein each of the extensions extends beyond a recessed portion of the side wall.

17. The system according to claim 13, wherein the engagement portion of the drive shaft has a spherical shape flattened on opposite sides thereof.

18. The system according to claim 17, wherein the spherical shape of the engagement portion of the drive shaft includes a greatest diameter of the sphere.

19. The system according to claim 13, wherein the device is configured to rotate the intervertebral implant about a symmetrical center point of the hollow space via the drive shaft which may follow a path of the elongate opening of the intervertebral implant, and/or via the engagement structure sliding along a path defined by the at least two guiding surfaces.

20. The system according to claim 13, wherein the spherical segment shape of the hollow space formed within the intervertebral implant forms an abutment against which an end face of the engagement portion of the drive shaft is configured to abut.

21. The system according to claim 13, wherein a region of the intervertebral implant that defines the spherical segment shape of the hollow space is formed monolithically with the side wall that defines the elongate opening.

22. The system according to claim 13, wherein when the engagement portion of the drive shaft is received in the hollow space through the elongate opening and rotated by an angle about the longitudinal axis such that the engagement portion is supported in the hollow space, the intervertebral implant is rotatable relative to the device about a second axis perpendicular to the longitudinal axis of the sleeve.

23. The system according to claim 22, wherein the second axis extends through a center of the sphere defined by the spherical segment shape of the hollow space formed within the intervertebral implant.

24. A system comprising an intervertebral implant and a device to insert the intervertebral implant into a body, the intervertebral implant comprising a top surface, a bottom surface, and a side wall extending between the top surface and the bottom surface, the intervertebral implant having a hollow space having a spherical segment shape formed within the intervertebral implant and accessible through an elongate opening extending through the side wall, a recessed portion of the side wall being defined by wall portions extending inwardly from an outer contour of the intervertebral implant to the hollow space, the elongate opening extending between the wall portions, the intervertebral implant further comprising at least two guiding surfaces extending along an end of the intervertebral implant in an arc-shaped manner and facing one another such that the elongate opening extends therebetween, wherein the device comprises:

a drive shaft including an engagement portion configured to engage the intervertebral implant in the hollow space; and a sleeve movably holding and guiding the drive shaft and having a longitudinal axis, wherein the sleeve comprises an engagement structures;

wherein when the engagement portion of the drive shaft is received in the hollow space through the elongate opening and rotated by an angle about the longitudinal axis such that the engagement portion is supported in the hollow space, the engagement structure of the sleeve is configured to engage and slide laterally along the arc-shape of the at least two guiding surfaces, while being shaped to prevent rotation of the sleeve relative to the at least two guiding surfaces about the longitudinal axis.

25. The system according to claim 24, wherein the hollow space has a center point, and wherein each of the at least two guiding surfaces includes a first portion at which the outer contour is concentric about a longitudinal axis of the intervertebral implant extending through the center point, and each of the at least two guiding surfaces further includes a second portion at which the outer contour is recessed from a concentric shape about the longitudinal axis of the intervertebral implant, such that a radial distance from the outer contour at the second portion to the longitudinal axis of the intervertebral implant is less than a radial distance from the outer contour at the first portion to the longitudinal axis of the intervertebral implant to allow latching-in of a portion of the sleeve.

26. The system according to claim 25, wherein at the second portion, the outer contour extends in a straight direction.

27. The system according to claim 25, wherein a distal end face of the sleeve has a substantially annular shape and comprises:

a planar surface portion configured to engage the second portion of a guiding surface of the at least two guiding surfaces which extends in a straight direction; and a concave surface portion having a curvature corresponding to the first portion of each of the at least two guiding surfaces.

28. The system according to claim 24, wherein at least one of the top surface or the bottom surface has a hole to allow visual access to the engagement portion in the hollow space.

29. The system according to claim 24, wherein the engagement structure includes at least one projection extending from a distal end face of the sleeve in a direction along the longitudinal axis of the sleeve, wherein the at least one projection defines two guiding faces arranged at respective ends of the at least one projection in a circumferential direction and spaced at a first distance from each other corresponding to a second distance between the at least two guiding surfaces.

30. The system according to claim 24, wherein the drive shaft is rotatable with respect to the sleeve about the longitudinal axis of the sleeve.

31. A method of inserting an intervertebral implant into a body using a device, the intervertebral implant comprising a top surface, a bottom surface, and a side wall extending between the top surface and the bottom surface, the intervertebral implant having a hollow space having a spherical segment shape formed within the intervertebral implant and accessible through an elongate opening extending through the side wall at an end of the intervertebral implant, the intervertebral implant further comprising at least two guiding surfaces extending along the end of the intervertebral implant in an arc-shaped manner and facing one another, the device comprising a drive shaft including an engagement portion configured to engage the intervertebral implant in the hollow space, and a sleeve movably holding and guiding the drive shaft and having a longitudinal axis, the sleeve comprising an engagement structure, the method comprising:

inserting the engagement portion of the drive shaft through the elongate opening into the hollow space; and rotating the engagement portion by an angle about the longitudinal axis such that the engagement portion is supported in the hollow space, while the engagement structure of the sleeve engages and is configured to slide laterally along the arc-shape of the at least two guiding surfaces, while being shaped to prevent rotation of the sleeve relative to the at least two guiding surfaces about the longitudinal axis.

32. The method according to claim 31, further comprising sliding the engagement structure along the at least two guiding surfaces.

* * * * *

UNITED STATES PATENT AND TRADEMARK OFFICE
CERTIFICATE OF CORRECTION

PATENT NO. : 10,376,374 B2  
APPLICATION NO. : 15/246448  
DATED : August 13, 2019  
INVENTOR(S) : Timo Biedermann et al.

Page 1 of 1

It is certified that error appears in the above-identified patent and that said Letters Patent is hereby corrected as shown below:

In the Specification  
Column 1, Line 62 after "cuboid-" delete "Ss"  
Column 2, Line 13 delete "patients" and insert -- patient's --  
Column 5, Line 27 delete "5A," and insert -- 2A, --  
Column 5, Line 48 delete "view:" and insert -- view; --  
Column 6, Line 6 delete "side:" and insert -- side; --  
Column 6, Line 29 delete "18A," and insert -- 16A, --  
Column 7, Line 5 delete "aides" and insert -- sides --  
Column 7, Line 7 delete "63" and insert -- 53 --  
Column 7, Lines 21-22 delete "(protrusion 58') is as" and insert -- (protrusion 56') is --  
Column 7, Line 34 delete "Into" and insert -- into --  
Column 8, Line 32 delete "56," and insert -- 5b, --  
Column 10, Line 59 delete "Incorporated" and insert -- incorporated --  
Column 11, Line 58 delete "sidewall" and insert -- side wall --  
Column 13, Line 31 delete "result. In" and insert -- result, in --  
Column 13, Line 37 delete "arc shaped" and insert -- arc-shaped --  
Column 16, Line 5 delete "Implant" and insert -- implant --  
Column 16, Line 19 delete "Implant" and insert -- implant --

In the Claims  
Column 16, Line 51, Claim 1 delete "structures;" and insert -- structure; --  
Column 18, Line 3, Claim 13 delete "structures;" and insert -- structure; --  
Column 19, Line 15 (approx.), Claim 24 delete "structures;" and insert -- structure; --

Signed and Sealed this  
Fourteenth Day of July, 2020

Andrei Iancu  
*Director of the United States Patent and Trademark Office*